US012714323B2

(12) United States Patent
Li et al.

(10) Patent No.: US 12,714,323 B2
(45) Date of Patent: Aug. 25, 2026

(54) HEART RHYTHM DETECTION METHOD AND ELECTRONIC DEVICE

(71) Applicant: HONOR DEVICE CO., LTD., Shenzhen (CN)

(72) Inventors: Danhong Li, Shenzhen (CN); Haoxuan Di, Shenzhen (CN); Xiaowu Zhang, Shenzhen (CN); Ruiqing Ma, Shenzhen (CN)

(73) Assignee: HONOR DEVICE CO., LTD., Shenzhen (CN)

( * ) Notice: Subject to any disclaimer, the term of this patent is extended or adjusted under 35 U.S.C. 154(b) by 41 days.

(21) Appl. No.: 18/266,673

(22) PCT Filed: Dec. 20, 2022

(86) PCT No.: PCT/CN2022/140421

§ 371 (c)(1),
(2) Date: Jun. 12, 2023

(87) PCT Pub. No.: WO2023/185122

PCT Pub. Date: Oct. 5, 2023

(65) Prior Publication Data

US 2024/0215840 A1 Jul. 4, 2024

(30) Foreign Application Priority Data

Mar. 31, 2022 (CN) ......................... 202210335776.3

(51) Int. Cl.
*A61B 5/024* (2006.01)
*A61B 5/00* (2006.01)

(52) U.S. Cl.
CPC .......... *A61B 5/02427* (2013.01); *A61B 5/681* (2013.01); *A61B 5/7246* (2013.01);
(Continued)

(58) Field of Classification Search
None
See application file for complete search history.

(56) References Cited

U.S. PATENT DOCUMENTS 10,039,469 B2 8/2018 Higgins et al.
2004/0092836 A1 5/2004 Ritscher et al.
(Continued)

FOREIGN PATENT DOCUMENTS

CN 105816163 A 8/2016
CN 106037701 A 10/2016
(Continued)

OTHER PUBLICATIONS

Bashar et al., "Atrial Fibrillation Detection from Wrist Photoplethysmography Signals Using Smartwatches," (Oct. 21, 2019), Scientific Reports vol. 9, Article No. 15054. (Year: 2019).*
(Continued)

*Primary Examiner* — Keith M Raymond
*Assistant Examiner* — Ashish S. Jasani
(74) *Attorney, Agent, or Firm* — WOMBLE BOND DICKINSON (US) LLP

(57) ABSTRACT

A heart rate detection method and an electronic device are provided. The method includes: acquiring a first PPG signal with a first preset duration; determining a plurality of heart rate values based on the first PPG signal; determining a difference of every two adjacent heart rates based on the plurality of heart rate values, the difference of every two adjacent heart rates being used for generating a heart rate difference trajectory graph; acquiring a parameter of a heart rate difference trajectory based on the heart rate difference trajectory graph, the parameter of the heart rate difference trajectory including one or more of the following parameters: an angle, a quantity, an angle standard deviation, and a distance standard deviation; determining a heart rhythm
(Continued)

type of the first PPG signal according to the parameter of the heart rate difference trajectory; and displaying the heart rhythm type of the first PPG signal.

20 Claims, 12 Drawing Sheets

(52) U.S. Cl.
CPC .......... *A61B 5/7282* (2013.01); *A61B 5/7285* (2013.01); *A61B 5/743* (2013.01); *A61B 5/7435* (2013.01)

(56) References Cited

U.S. PATENT DOCUMENTS

| | | | | |
|---|---|---|---|---|
| 2011/0301480 | A1 | 12/2011 | Ghanem et al. | |
| 2014/0330134 | A1* | 11/2014 | Chon | A61B 5/361 600/479 |
| 2016/0302736 | A1 | 10/2016 | Koyama et al. | |
| 2018/0104502 | A1 | 4/2018 | Perschbacher et al. | |
| 2018/0256059 | A1 | 9/2018 | Perschbacher et al. | |
| 2019/0167142 | A1 | 6/2019 | Perschbacher et al. | |
| 2019/0298201 | A1 | 10/2019 | Persen et al. | |
| 2019/0374117 | A1 | 12/2019 | Liao et al. | |

FOREIGN PATENT DOCUMENTS

| | | | |
|---|---|---|---|
| CN | 109069050 | A | 12/2018 |
| CN | 110575152 | A | 12/2019 |
| CN | 110960203 | A | 4/2020 |
| CN | 113491508 | A | 10/2021 |
| WO | 2021244367 | A1 | 12/2021 |

OTHER PUBLICATIONS

Han Dong et al: “Premature Atrialand Ventricular Contraction Detection Using Photoplethysmographic Data from a Smartwatch”, Sensors, vol. 20, No. 19, Oct. 5, 2020 (Oct. 5, 2020), p. 5683.

Luo Chengsi et al: “An improved Poincaré plot-based method to dete atrialfibrillation from short single-lead ECG”, Biomedical Alsignal Processing and Control, vol. 64, Oct. 26, 2020 (Oct. 26, 2020), p. 102264.

Parsi Ashkan et al: “Prediction of paroxysmal atrial fibrillation using new heart rate variability features”, Computers in Biology and Medicine, Newyork, NY, US, vol. 133, Apr. 2, 2021 (Apr. 2, 2021), total 11 pages.

Syed Khairul Bashar et al: “Atrial Fibrillation Detection from Wrist Photoplethysmography Signals Using Smartwatches”, Scientific Reports,vol. 9, No. 1, Oct. 21, 2019 (Oct. 21, 2019), pp. 1-10.

Jing Yongming ; Towards Jintao ; Principles and applications of analytical geometry formed by difference scatter plots ; Chinese Journal of Cardiac Pacing and Cardiac Electrophysiology; Classification No. R541.7;Apr. 10, 2013; 2 pages.

* cited by examiner

Premature beat

Normal atrial fibrillation

Rapid atrial fibrillation 2 5 7

ΔHRn 0 6 0 1

8 3 4

0

ΔHRn+1

Sinus rhythm

Premature beat with bigeminy

Premature beat with trigeminy

CONT. FROM FIG. 11A

FIG. 11B

HEART RHYTHM DETECTION METHOD AND ELECTRONIC DEVICE

CROSS-REFERENCE TO RELATED APPLICATIONS

This application is a national stage of International Application No. PCT/CN2022/140421, filed on Dec. 20, 2022, which claims priority to Chinese Patent Application No. 202210335776.3, filed on Mar. 31, 2022. The disclosures of both of the aforementioned applications are hereby incorporated by reference in their entireties.

TECHNICAL FIELD

This application relates to the field of terminal technologies, and specifically, to a heart rhythm detection method and an electronic device.

BACKGROUND

As an age of onset of a heart disease gradually tends to be younger and normalized, heart health has attracted more and more attention. An arrhythmia may include atrial fibrillation, a premature beat, and the like. The atrial fibrillation is a common heart disease. Early recognition of the atrial fibrillation could help patients find heart abnormalities in time. The premature beat is a common arrhythmia.

Medically, a 24-hour dynamic electrocardiogram is generally acquired by using Holter. However, this detection method requires professional assistance, a complex operation, and a high cost. In particular, paroxysmal atrial fibrillation and an occasional ventricular premature beat have short onset time and uncertain timing, which easily causes missed detection of "no disease at the time of detection, no detection at the time of a disease". To save costs and facilitate user operations, measurement of the arrhythmia is generally implemented by a photoplethysmograph (photoplethysmograph, PPG) technology. For example, a user may detect the arrhythmia through a smart watch.

However, in a practical application, a PPG signal is prone to misrecognition (for example, a premature beat signal is recognized as an atrial fibrillation signal), so that the atrial fibrillation or premature beat cannot be accurately recognized, which affects user experience.

SUMMARY

In view of the above, this application provides a heart rhythm detection method, an electronic device, a computer-readable storage medium, and a computer program product, which can improve accuracy of detection of the arrhythmia and greatly improve the user experience.

According to a first aspect, a heart rhythm detection method is provided. The method is applied to an electronic device, and includes:

- acquiring a first PPG signal with a first preset duration;
- determining a plurality of heart rate values based on the first PPG signal;
- determining a difference of every two adjacent heart rates based on the plurality of heart rate values, the difference of every two adjacent heart rates being used for generating a heart rate difference trajectory graph;
- acquiring a parameter of a heart rate difference trajectory based on the heart rate difference trajectory graph, the parameter of the heart rate difference trajectory including one or more of the following parameters: an angle, a quantity, an angle standard deviation, and a distance standard deviation;
- determining a heart rhythm type of the first PPG signal according to the parameter of the heart rate difference trajectory, the heart rhythm type including any one of the following: a premature beat, atrial fibrillation, a sinus rhythm, ventricular tachycardia, bigeminy, and trigeminy; and
- displaying the heart rhythm type of the first PPG signal.

The above method may be performed by an electronic device or a chip in the electronic device. Based on the above solution, the PPG signal with the first preset duration is acquired, according to a trajectory of changes in a heart rate difference of the PPG signal with the first preset duration, a parameter (including, but not limited to, an angle, a quantity, an angle standard deviation, and a distance standard deviation) of the trajectory is obtained, a heart rhythm type is then determined based on the parameter of the trajectory, and the heart rhythm type is presented to a user. According to this embodiment of this application, recognition of a heart rhythm type based on a parameter derived from a heart rate difference trajectory can improve the accuracy of detection of the arrhythmia. In addition, compared with heart rhythm recognition based on each heart rate (or a cardiac waveform), according to this embodiment of this application, heart rate recognition is based on a heart rate of a signal (that is, the PPG signal with the first preset duration), which can improve accuracy of recognition of the premature beat or atrial fibrillation, reduce a probability of recognizing the premature beat as the atrial fibrillation, and improve user experience.

In a possible implementation, the method further includes:

- determining a first parameter according to the first PPG signal with the first preset duration, and determining whether the first parameter is greater than or equal to a first threshold;
- where the determining a heart rhythm type of the first PPG signal according to the parameter of the heart rate difference trajectory includes:
- determining the heart rhythm type of the first PPG signal according to the first parameter and the parameter of the heart rate difference trajectory.

Optionally, the determining a first parameter according to the PPG signal with the first preset duration includes: extracting a plurality of RRIs according to a peak of the PPG signal with the first preset duration; and calculating a difference between every two adjacent RRIs according to the plurality of RRIs, the difference between every two adjacent RRIs being used for determining the first parameter.

Herein, comparison of a size relationship between the first parameter and the first threshold is to perform preliminary recognition of atrial fibrillation. If the first parameter is greater than or equal to the first threshold, a probability of atrial fibrillation is greater than a probability of non-atrial fibrillation in this case, and then first recognition is entered. If the first parameter is less than the first threshold, the probability of atrial fibrillation is less than the probability of non-atrial fibrillation in this case, and then second recognition is entered. In this way, a data flow can be split to save a subsequent judgment procedure, thereby saving power consumption of the electronic device. For example, in a case of a non-atrial fibrillation recognition window, a procedure of determining whether the bigeminy or trigeminy occurs may be involved in the following, while a judgment procedure in an atrial fibrillation recognition window may not be involved.

In a possible implementation, the determining the heart rhythm type of the first PPG signal according to the first parameter and the parameter of the heart rate difference trajectory includes:

performing, when the first parameter is greater than or equal to the first threshold, first recognition based on the parameter of the heart rate difference trajectory to determine the heart rhythm type of the first PPG signal, the heart rhythm type including any one of the following: the premature beat, the atrial fibrillation, the sinus rhythm, and the ventricular tachycardia; and performing, when the first parameter is less than the first threshold, second recognition based on the parameter of the heart rate difference trajectory to determine the heart rhythm type of the first PPG signal, the heart rhythm type including any one of the following: the premature beat, the atrial fibrillation, the sinus rhythm, the ventricular tachycardia, the bigeminy, and the trigeminy.

In a possible implementation, in the first recognition or the second recognition, the heart rate difference trajectory includes: a first trajectory and a second trajectory; and the heart rhythm type is the premature beat when a parameter of the first trajectory and a parameter of the second trajectory meet a first preset condition;

where that a parameter of the first trajectory and a parameter of the second trajectory meet a first preset condition includes: a sum of a quantity parameter of the first trajectory and a quantity parameter of the second trajectory being greater than or equal to a first quantity threshold, and an angle standard deviation parameter of the first trajectory and an angle standard deviation parameter of the second trajectory being both less than or equal to a first angle standard deviation threshold.

Multiple implementations of determining the heart rhythm type based on the parameter of the heart rhythm difference trajectory and a related preset condition are described below.

In a possible implementation, in the first recognition, the heart rate difference trajectory includes: the first trajectory and the second trajectory; and the heart rhythm type is the atrial fibrillation when the parameter of the first trajectory and the parameter of the second trajectory meet a second preset condition and a first probability parameter meets a third preset condition;

where that the parameter of the first trajectory and the parameter of the second trajectory meet a second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold;

where that a first probability parameter meets a third preset condition includes: the first probability parameter being less than a first probability threshold.

In a possible implementation, the heart rate difference trajectory includes: the first trajectory and the second trajectory; and the heart rhythm type is the sinus rhythm when the parameter of the first trajectory and the parameter of the second trajectory meet the second preset condition and the first probability parameter does not meet the third preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold;

where that the first probability parameter does not meet the third preset condition includes: the first probability parameter being no less than the first probability threshold.

In a possible implementation, in the first recognition or the second recognition, the heart rate difference trajectory includes: the first trajectory, the second trajectory, a third trajectory, and a fourth trajectory; and when the parameter of the first trajectory and the parameter of the second trajectory meet a fourth preset condition and the parameter of the first trajectory and a parameter of the third trajectory meet a fifth preset condition; or when the parameter of the first trajectory and the parameter of the second trajectory meet a fourth preset condition and the parameter of the second trajectory and a parameter of the fourth trajectory meet a sixth preset condition, the heart rhythm type is the ventricular tachycardia;

where that the parameter of the first trajectory and the parameter of the second trajectory meet a fourth preset condition includes: the sum of the quantity parameter of the first trajectory and the quantity parameter of the second trajectory being less than the first quantity threshold;

where that the parameter of the first trajectory and a parameter of the third trajectory meet a fifth preset condition includes: a sum of the quantity parameter of the first trajectory and a quantity parameter of the third trajectory being greater than or equal to a second quantity threshold, the angle standard deviation parameter of the first trajectory and an angle standard deviation parameter of the third trajectory being both less than or equal to a second angle standard deviation threshold, and an angle mean parameter of the first trajectory being less than that of the third trajectory;

where that the parameter of the second trajectory and a parameter of the fourth trajectory meet a sixth preset condition includes: a sum of the quantity parameter of the second trajectory and the quantity parameter of the third trajectory being greater than or equal to the second quantity threshold, the angle standard deviation parameter of the second trajectory and the angle standard deviation parameter of the third trajectory being both less than or equal to the second angle standard deviation threshold, and an angle mean parameter of the second trajectory being less than that of the fourth trajectory.

In a possible implementation, in the first recognition, the heart rate difference trajectory includes: the first trajectory and the second trajectory; and the heart rhythm type is the atrial fibrillation when the parameter of the first trajectory and the parameter of the second trajectory meet the fourth preset condition and the first probability parameter meets a seventh preset condition;

where that the parameter of the first trajectory and the parameter of the second trajectory meet the fourth preset condition includes: the sum of the quantity parameter of the first trajectory and the quantity parameter of the second trajectory being less than the first quantity threshold;

where that the first probability parameter meets a seventh preset condition includes: the first probability parameter being less than a second probability threshold.

In a possible implementation, in the first recognition, the heart rate difference trajectory includes: the first trajectory and the second trajectory; and the heart rhythm type is the sinus rhythm when the parameter of the first trajectory and the parameter of the second trajectory meet the fourth preset condition and the first probability parameter does not meet the seventh preset condition;

where that the parameter of the first trajectory and the parameter of the second trajectory meet the fourth preset condition includes: the sum of the quantity parameter of the first trajectory and the quantity parameter of the second trajectory being less than the first quantity threshold;

where that the first probability parameter does not meet the seventh preset condition includes: the first probability parameter being no less than the second probability threshold.

In a possible implementation, in the second recognition, the heart rate difference trajectory includes: the first trajectory and the second trajectory; and the heart rhythm type is the atrial fibrillation when the parameter of the first trajectory and the parameter of the second trajectory meet the second preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold.

In a possible implementation, in the second recognition, the heart rate difference trajectory includes: a fifth trajectory and a sixth trajectory; and the heart rhythm type is the bigeminy when a parameter of the fifth trajectory and a parameter of the sixth trajectory meet an eighth preset condition and a distance standard deviation parameter of the fifth trajectory and a distance standard deviation parameter of the sixth trajectory meet a ninth preset condition;

where that a parameter of the fifth trajectory and a parameter of the sixth trajectory meet an eighth preset condition includes: a minimum value of a quantity parameter of the fifth trajectory and a quantity parameter of the sixth trajectory being greater than or equal to a third quantity threshold, and an angle standard deviation parameter of the fifth trajectory and an angle standard deviation parameter of the sixth trajectory being both less than or equal to a third angle standard deviation threshold.

where that a distance standard deviation parameter of the fifth trajectory and a distance standard deviation parameter of the sixth trajectory meet a ninth preset condition includes: the distance standard deviation parameter of the fifth trajectory being less than or equal to a first distance standard deviation threshold, and the distance standard deviation parameter of the sixth trajectory being less than or equal to the first distance standard deviation threshold.

Therefore, based on the heart rhythm detection method according to this embodiment of this application, the bigeminy can be accurately recognized, and the user experience can be improved.

In a possible implementation, in the second recognition, the heart rate difference trajectory includes: the fifth trajectory and the sixth trajectory; the heart rhythm type is the trigeminy when the parameter of the fifth trajectory and the parameter of the sixth trajectory meet the eighth preset condition and the distance standard deviation parameter of the fifth trajectory and the distance standard deviation parameter of the sixth trajectory do not meet the ninth preset condition;

where that the parameter of the fifth trajectory and the parameter of the sixth trajectory meet the eighth preset condition includes: the minimum value of the quantity parameter of the fifth trajectory and the quantity parameter of the sixth trajectory being greater than or equal to the third quantity threshold, and the angle standard deviation parameter of the fifth trajectory and the angle standard deviation parameter of the sixth trajectory being both less than or equal to the third angle standard deviation threshold;

where that the distance standard deviation parameter of the fifth trajectory and the distance standard deviation parameter of the sixth trajectory do not meet the ninth preset condition includes: the distance standard deviation parameter of the fifth trajectory being greater than the first distance standard deviation threshold, and the distance standard deviation parameter of the sixth trajectory being greater than the first distance standard deviation threshold.

Therefore, based on the heart rhythm detection method according to this embodiment of this application, the trigeminy can be accurately recognized, and the user experience can be improved.

In a possible implementation, in the second recognition, the heart rate difference trajectory includes: the first trajectory, the second trajectory, a seventh trajectory, an eighth trajectory, a ninth trajectory, and a tenth trajectory; and the heart rhythm type is the premature beat when the parameter of the first trajectory and the parameter of the second trajectory meet the second preset condition and a parameter of the seventh trajectory, a parameter of the eighth trajectory, a parameter of the ninth trajectory, and a parameter of the tenth trajectory meet a tenth preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than a first standard deviation threshold;

where that a parameter of the seventh trajectory, a parameter of the eighth trajectory, a parameter of the ninth trajectory, and a parameter of the tenth trajectory meet a tenth preset condition includes: a maximum value of an angle standard deviation parameter of the seventh trajectory, an angle standard deviation parameter of the eighth trajectory, an angle standard deviation parameter of the ninth trajectory, and an angle standard deviation parameter of the tenth trajectory being less than or equal to a fourth angle standard deviation threshold.

In a possible implementation, in the second recognition, the heart rate difference trajectory includes: the first trajectory, the second trajectory, the seventh trajectory, the eighth trajectory, the ninth trajectory, and the tenth trajectory; and the heart rhythm type is the atrial fibrillation when the parameter of the first trajectory and the parameter of the second trajectory meet the second preset condition, the parameter of the seventh trajectory, the parameter of the eighth trajectory, the parameter of the ninth trajectory, and the parameter of the tenth trajectory do not meet the tenth preset condition, and the first probability parameter meets an eleventh preset condition or a first quantity meets a twelfth preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

where that the parameter of the seventh trajectory, the parameter of the eighth trajectory, the parameter of the ninth trajectory, and the parameter of the tenth trajectory do not meet the tenth preset condition includes: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold;

where that the first probability parameter meets an eleventh preset condition includes: the first probability parameter being less than a third probability threshold;

where that a first quantity meets a twelfth preset condition includes: the first quantity being greater than or equal to a fourth quantity threshold.

In a possible implementation, in the second recognition, the heart rate difference trajectory includes: the first trajectory, the second trajectory, the seventh trajectory, the eighth trajectory, the ninth trajectory, and the tenth trajectory; and the heart rhythm type is the sinus rhythm when the parameter of the first trajectory and the parameter of the second trajectory meet the second preset condition, the parameter of the seventh trajectory, the parameter of the eighth trajectory, the parameter of the ninth trajectory, and the parameter of the tenth trajectory do not meet the tenth preset condition, and the first probability parameter does not meet the eleventh preset condition or the first quantity does not meet the twelfth preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

where that the parameter of the seventh trajectory, the parameter of the eighth trajectory, the parameter of the ninth trajectory, and the parameter of the tenth trajectory do not meet the tenth preset condition includes: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold;

where that the first probability parameter does not meet the eleventh preset condition includes: the first probability parameter being no less than the third probability threshold;

where that the first quantity does not meet the twelfth preset condition includes: the first quantity being less than the fourth quantity threshold.

In a possible implementation, the method further includes:

acquiring an ACC signal with a second preset duration; and determining a state of the electronic device based on the ACC signal with the second preset duration;

where the acquiring a first PPG signal with a first preset duration includes:

acquiring the first PPG signal with the first preset duration if the electronic device is always in a static state within a third preset duration, the third preset duration being less than or equal to the second preset duration.

Therefore, prior to acquisition of the PPG signal, the state of the electronic device can be determined by acquiring the ACC signal first, and an atrial fibrillation or premature beat detection algorithm is entered when the electronic device is in the static state, providing preparation for subsequent acquisition of the PPG signal.

In a possible implementation, the acquiring a first PPG signal with a first preset duration includes:

acquiring a PPG signal and an ACC signal with a fourth preset duration, the PPG signal with the first preset duration including a plurality of PPG signals with the fourth preset duration, the fourth preset duration being less than the first preset duration;

determining whether the electronic device has been in a motion state within the fifth preset duration; and continuously acquiring the PPG signal and the ACC signal with the fourth preset duration until an acquisition duration meets the first preset duration if the electronic device has not been in the motion state within the fifth preset duration.

Herein, the ACC signal can also be acquired while the PPG signal is acquired, and the state of the electronic device is determined based on the ACC signal, which is conducive to acquiring an active PPG signal.

In a possible implementation, the method further includes:

displaying prompt information to a user when the heart rhythm type is the atrial fibrillation, the prompt information being used for notifying the user of an abnormal heart rhythm.

Therefore, when an abnormal heart rhythm is detected, prompt information can be sent to the user, so that the user can know a risk of the abnormal heart rhythm in time.

According to a second aspect, an electronic device is provided, including units configured to perform any method according to the first aspect. The electronic device may be a wearable device (such as a smart watch or bracelet), or a chip in the wearable device (such as the smart watch or bracelet). The electronic device includes an input unit, a display unit, and a processing unit.

When the electronic device is the wearable device, the processing unit may be a processor, the input unit may be a communication interface, and the display unit may be a graphic processing module and screen. The wearable device may further include a memory, the memory being configured to store computer program codes, where the computer program codes stored in the memory, when executed by the processor, cause the wearable device to perform any method according to the first aspect.

When the electronic device is the chip in the wearable device, the processing unit may be a logic processing unit in the chip, the input unit may be an output interface, a pin, a circuit, or the like, and the display unit may be a graphic processing unit in the chip. The chip may further include a memory, and the memory may be a memory (such as a register or a cache) in the chip, or a memory (such as a read-only memory or a random access memory) located outside the chip. The memory is configured to store computer program codes, where the computer program codes stored in the memory, when executed by the processor, cause the chip to perform any method according to the first aspect.

Optionally, in an implementation, the processing unit is configured to acquire a first PPG signal with a first preset duration includes:

- determine a plurality of heart rate values based on the first PPG signal;
- determine a difference of every two adjacent heart rates based on the plurality of heart rate values, the difference of every two adjacent heart rates being used for generating a heart rate difference trajectory graph;
- acquire a parameter of a heart rate difference trajectory based on the heart rate difference trajectory graph, the parameter of the heart rate difference trajectory including one or more of the following parameters: an angle, a quantity, an angle standard deviation, and a distance standard deviation;
- determine a heart rhythm type of the first PPG signal according to the parameter of the heart rate difference trajectory, the heart rhythm type including any one of the following: a premature beat, atrial fibrillation, a sinus rhythm, ventricular tachycardia, bigeminy, and trigeminy.

The display unit is configured to display the heart rhythm type of the first PPG signal.

In a possible implementation, the processing unit is further configured to:

- determine a first parameter according to the first PPG signal with the first preset duration, and determining whether the first parameter is greater than or equal to a first threshold;
- determine the heart rhythm type of the first PPG signal according to the first parameter and the parameter of the heart rate difference trajectory.

Optionally, that the processing unit is configured to determine a first parameter according to the PPG signal with the first preset duration specifically includes: extracting a plurality of RRIs according to a peak of the PPG signal with the first preset duration; and calculating a difference between every two adjacent RRIs according to the plurality of RRIs, the difference between every two adjacent RRIs being used for determining the first parameter.

In a possible implementation, that the processing unit is configured to determine the heart rhythm type of the first PPG signal according to the first parameter and the parameter of the heart rate difference trajectory specifically includes:

- performing, when the first parameter is greater than or equal to the first threshold, first recognition based on the parameter of the heart rate difference trajectory to determine the heart rhythm type of the first PPG signal, the heart rhythm type including any one of the following: the premature beat, the atrial fibrillation, the sinus rhythm, and the ventricular tachycardia; and
- performing, when the first parameter is less than the first threshold, second recognition based on the parameter of the heart rate difference trajectory to determine the heart rhythm type of the first PPG signal, the heart rhythm type including any one of the following: the premature beat, the atrial fibrillation, the sinus rhythm, the ventricular tachycardia, the bigeminy, and the trigeminy.

In a possible implementation, in the first recognition or the second recognition, the heart rate difference trajectory includes: a first trajectory and a second trajectory; and the heart rhythm type is the premature beat when a parameter of the first trajectory and a parameter of the second trajectory meet a first preset condition;

- where that a parameter of the first trajectory and a parameter of the second trajectory meet a first preset condition includes: a sum of a quantity parameter of the first trajectory and a quantity parameter of the second trajectory being greater than a first quantity threshold, and an angle standard deviation parameter of the first trajectory and an angle standard deviation parameter of the second trajectory being both less than or equal to a first angle standard deviation threshold.

In a possible implementation, in the first recognition, the heart rate difference trajectory includes: the first trajectory and the second trajectory; and the heart rhythm type is the atrial fibrillation when the parameter of the first trajectory and the parameter of the second trajectory meet the first preset condition and a first probability parameter meets a third preset condition;

- where that the parameter of the first trajectory and the parameter of the second trajectory meet the first preset condition includes: the sum of the quantity parameter of the first trajectory and the quantity parameter of the second trajectory being greater than the first quantity threshold, and the angle standard deviation parameter of the first trajectory and the angle standard deviation parameter of the second trajectory being both less than or equal to the first angle standard deviation threshold;
- where that a first probability parameter meets a third preset condition includes: the first probability parameter being less than a first probability threshold.

In a possible implementation, the heart rate difference trajectory includes: the first trajectory and the second trajectory; and the heart rhythm type is the sinus rhythm when the parameter of the first trajectory and the parameter of the second trajectory meet the second preset condition and the first probability parameter does not meet the third preset condition;

- where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold;

where that the first probability parameter does not meet the third preset condition includes: the first probability parameter being no less than the first probability threshold.

In a possible implementation, in the first recognition or the second recognition, the heart rate difference trajectory includes: the first trajectory, the second trajectory, a third trajectory, and a fourth trajectory; and when the parameter of the first trajectory and the parameter of the second trajectory meet a fourth preset condition and the parameter of the first trajectory and a parameter of the third trajectory meet a fifth preset condition; or when the parameter of the first trajectory and the parameter of the second trajectory meet a fourth preset condition and the parameter of the second trajectory and a parameter of the fourth trajectory meet a sixth preset condition, the heart rhythm type is the ventricular tachycardia;

where that the parameter of the first trajectory and the parameter of the second trajectory meet a fourth preset condition includes: the sum of the quantity parameter of the first trajectory and the quantity parameter of the second trajectory being less than the first quantity threshold;

where that the parameter of the first trajectory and a parameter of the third trajectory meet a fifth preset condition includes: a sum of the quantity parameter of the first trajectory and a quantity parameter of the third trajectory being greater than or equal to a second quantity threshold, the angle standard deviation parameter of the first trajectory and an angle standard deviation parameter of the third trajectory being both less than or equal to a second angle standard deviation threshold, and an angle mean parameter of the first trajectory being less than that of the third trajectory;

where that the parameter of the second trajectory and a parameter of the fourth trajectory meet a sixth preset condition includes: a sum of the quantity parameter of the second trajectory and the quantity parameter of the third trajectory being greater than or equal to the second quantity threshold, the angle standard deviation parameter of the second trajectory and the angle standard deviation parameter of the third trajectory being both less than or equal to the second angle standard deviation threshold, and an angle mean parameter of the second trajectory being less than that of the fourth trajectory.

In a possible implementation, in the first recognition, the heart rate difference trajectory includes: the first trajectory and the second trajectory; and the heart rhythm type is the atrial fibrillation when the parameter of the first trajectory and the parameter of the second trajectory meet the fourth preset condition and the first probability parameter meets a seventh preset condition;

where that the parameter of the first trajectory and the parameter of the second trajectory meet the fourth preset condition includes: the sum of the quantity parameter of the first trajectory and the quantity parameter of the second trajectory being less than the first quantity threshold;

where that the first probability parameter meets a seventh preset condition includes: the first probability parameter being less than a second probability threshold.

In a possible implementation, in the first recognition, the heart rate difference trajectory includes: the first trajectory and the second trajectory; and the heart rhythm type is the sinus rhythm when the parameter of the first trajectory and the parameter of the second trajectory meet the fourth preset condition and the first probability parameter does not meet the seventh preset condition;

where that the parameter of the first trajectory and the parameter of the second trajectory meet the fourth preset condition includes: the sum of the quantity parameter of the first trajectory and the quantity parameter of the second trajectory being less than the first quantity threshold;

where that the first probability parameter does not meet the seventh preset condition includes: the first probability parameter being no less than the second probability threshold.

In a possible implementation, in the second recognition, the heart rate difference trajectory includes: the first trajectory and the second trajectory; and the heart rhythm type is the atrial fibrillation when the parameter of the first trajectory and the parameter of the second trajectory meet the second preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold.

In a possible implementation, in the second recognition, the heart rate difference trajectory includes: a fifth trajectory and a sixth trajectory; the heart rhythm type is the bigeminy when a parameter of the fifth trajectory and a parameter of the sixth trajectory meet an eighth preset condition and a distance standard deviation parameter of the fifth trajectory and a distance standard deviation parameter of the sixth trajectory meet a ninth preset condition;

where that a parameter of the fifth trajectory and a parameter of the sixth trajectory meet an eighth preset condition includes: a minimum value of a quantity parameter of the fifth trajectory and a quantity parameter of the sixth trajectory being greater than or equal to a third quantity threshold, and an angle standard deviation parameter of the fifth trajectory and an angle standard deviation parameter of the sixth trajectory being both less than or equal to a third angle standard deviation threshold;

where that a distance standard deviation parameter of the fifth trajectory and a distance standard deviation parameter of the sixth trajectory meet a ninth preset condition includes: the distance standard deviation parameter of the fifth trajectory being less than or equal to a first distance standard deviation threshold, and the distance standard deviation parameter of the sixth trajectory being less than or equal to the first distance standard deviation threshold.

In a possible implementation, in the second recognition, the heart rate difference trajectory includes: the fifth trajectory and the sixth trajectory; the heart rhythm type is the trigeminy when the parameter of the fifth trajectory and the parameter of the sixth trajectory meet the eighth preset condition and the distance standard deviation parameter of the fifth trajectory and the distance standard deviation parameter of the sixth trajectory do not meet the ninth preset condition;

where that the parameter of the fifth trajectory and the parameter of the sixth trajectory meet the eighth preset condition includes: the minimum value of the quantity parameter of the fifth trajectory and the quantity parameter of the sixth trajectory being greater than or equal to the third quantity threshold, and the angle standard deviation parameter of the fifth trajectory and the angle standard deviation parameter of the sixth trajectory being both less than or equal to the third angle standard deviation threshold;

where that the distance standard deviation parameter of the fifth trajectory and the distance standard deviation parameter of the sixth trajectory do not meet the ninth preset condition includes: the distance standard deviation parameter of the fifth trajectory being greater than the first distance standard deviation threshold, and the distance standard deviation parameter of the sixth trajectory being greater than the first distance standard deviation threshold.

In a possible implementation, in the second recognition, the heart rate difference trajectory includes: the first trajectory, the second trajectory, a seventh trajectory, an eighth trajectory, a ninth trajectory, and a tenth trajectory; and the heart rhythm type is the premature beat when the parameter of the first trajectory and the parameter of the second trajectory meet the second preset condition and a parameter of the seventh trajectory, a parameter of the eighth trajectory, a parameter of the ninth trajectory, and a parameter of the tenth trajectory meet a tenth preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

where that a parameter of the seventh trajectory, a parameter of the eighth trajectory, a parameter of the ninth trajectory, and a parameter of the tenth trajectory meet a tenth preset condition includes: a maximum value of an angle standard deviation parameter of the seventh trajectory, an angle standard deviation parameter of the eighth trajectory, an angle standard deviation parameter of the ninth trajectory, and an angle standard deviation parameter of the tenth trajectory being less than or equal to a fourth angle standard deviation threshold.

In a possible implementation, in the second recognition, the heart rate difference trajectory includes: the first trajectory, the second trajectory, the seventh trajectory, the eighth trajectory, the ninth trajectory, and the tenth trajectory; and the heart rhythm type is the atrial fibrillation when the parameter of the first trajectory and the parameter of the second trajectory meet the second preset condition, the parameter of the seventh trajectory, the parameter of the eighth trajectory, the parameter of the ninth trajectory, and the parameter of the tenth trajectory do not meet the tenth preset condition, and the first probability parameter meets an eleventh preset condition or a first quantity meets a twelfth preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

where that the parameter of the seventh trajectory, the parameter of the eighth trajectory, the parameter of the ninth trajectory, and the parameter of the tenth trajectory do not meet the tenth preset condition includes: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold;

where that the first probability parameter meets an eleventh preset condition includes: the first probability parameter being less than a third probability threshold;

where that a first quantity meets a twelfth preset condition includes: the first quantity being greater than or equal to a fourth quantity threshold.

In a possible implementation, in the second recognition, the heart rate difference trajectory includes: the first trajectory, the second trajectory, the seventh trajectory, the eighth trajectory, the ninth trajectory, and the tenth trajectory; and the heart rhythm type is the sinus rhythm when the parameter of the first trajectory and the parameter of the second trajectory meet the second preset condition, the parameter of the seventh trajectory, the parameter of the eighth trajectory, the parameter of the ninth trajectory, and the parameter of the tenth trajectory do not meet the tenth preset condition, and the first probability parameter does not meet the eleventh preset condition or the first quantity does not meet the twelfth preset condition;

where that the parameter of the first trajectory and the parameter of the second trajectory meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

where that the parameter of the seventh trajectory, the parameter of the eighth trajectory, the parameter of the ninth trajectory, and the parameter of the tenth trajectory do not meet the tenth preset condition includes: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold;

where that the first probability parameter does not meet the eleventh preset condition includes: the first probability parameter being no less than the third probability threshold;

where that the first quantity does not meet the twelfth preset condition includes: the first quantity being less than the fourth quantity threshold.

In a possible implementation, the processing unit is further configured to:

acquire an ACC signal with a second preset duration; and determine a state of the electronic device based on the ACC signal with the second preset duration; and acquire the first PPG signal with the first preset duration if the electronic device is always in a static state within a third preset duration, the third preset duration being less than or equal to the second preset duration.

In a possible implementation, that the processing unit is configured to acquire a first PPG signal with a first preset duration specifically includes:

acquiring a PPG signal and an ACC signal with a fourth preset duration, the PPG signal with the first preset duration including a plurality of PPG signals with the fourth preset duration, the fourth preset duration being less than the first preset duration;

determining whether the electronic device has been in a motion state within a fifth preset duration; and continuously acquiring the PPG signal and the ACC signal with the fourth preset duration until an acquisition duration meets the first preset duration if the electronic device has not been in the motion state within the fifth preset duration.

In a possible implementation, the processing unit is further configured to:

invoke the display unit to display prompt information to a user when the heart rhythm type is the atrial fibrillation, the prompt information being used for notifying the user of an abnormal heart rhythm.

According to a third aspect, a computer-readable storage medium is provided and stores computer program codes. The computer program codes, when run by an electronic device, cause the electronic device to perform any method in the first aspect.

According to a fourth aspect, a computer program product is provided, including: computer program codes, where the computer program codes, when run by an electronic device, cause the electronic device to perform any method according to the first aspect.

BRIEF DESCRIPTION OF DRAWINGS

FIG. 11A and FIG. 11B are an exemplary diagram of an interface of heart rhythm detection according to an embodiment of this application;

DESCRIPTION OF EMBODIMENTS

The following describes technical solutions in embodiments of this application with reference to the accompanying drawings.

The embodiments of this application are applicable to an electronic device. The electronic device may be a smart watch, a smart bracelet, a wristband, a helmet, a headband, glasses, another wearable device or medical detection device that can be configured to detect a heart rhythm or monitor a heart rate, or the like. The electronic device measures a pulse or a heart rate of a user by a photoplethysmograph (photoplethysmograph, PPG) technology. The electronic device may conduct wireless communication with another terminal in various wireless manners. The terminal includes, but is not limited to, a mobile phone, a tablet computer, a wireless communication device, a remote terminal, a mobile device, a user terminal, a handheld device with a wireless communication function, a computing device, another processing device connected to a wireless modem, an in-vehicle device, a wearable device, a terminal device in a future 5G or 6G network, and the like.

The principle of measuring a pulse or a heart rate by the PPG technology is as follows: Light of a specific color and wavelength is emitted into a human body through a light-emitting diode (light-emitting diode, LED), then attenuated light reflected and absorbed by human blood vessels and tissues is measured, and a pulse state of the blood vessels is traced, to achieve a purpose of detecting a pulse signal.

For example, the electronic device is a smart watch, and a heart rate sensor (for example, a PPG sensor or a PPG module) may be disposed in the smart watch. The smart watch acquires a PPG signal through the heart rate sensor and obtains an instantaneous heart rate of the user based on the PPG signal. The type of the heart rate sensor is not specifically limited in the embodiments of this application. For example, the heart rate sensor includes a reflective photoelectric heart rate sensor, a transmissive photoelectric heart rate sensor, and the like. In the embodiments of this application, the smart watch may detect a heart rhythm type based on the obtained PPG signal, so as to know whether a heart rhythm is a normal heart rhythm or an abnormal (or irregular) heart rhythm. It may be understood that the foregoing is only described by taking a smart watch as an example, but the embodiments of the application are not limited thereto.

The embodiments of this application are also applicable to a terminal. For example, the terminal acquires, through a smart watch, a PPG signal measured by the watch. Optionally, the terminal, after obtaining the PPG signal measured by the smart watch, may also determine a heart rhythm type by using the method according to the embodiments of this application.

Figure 1:
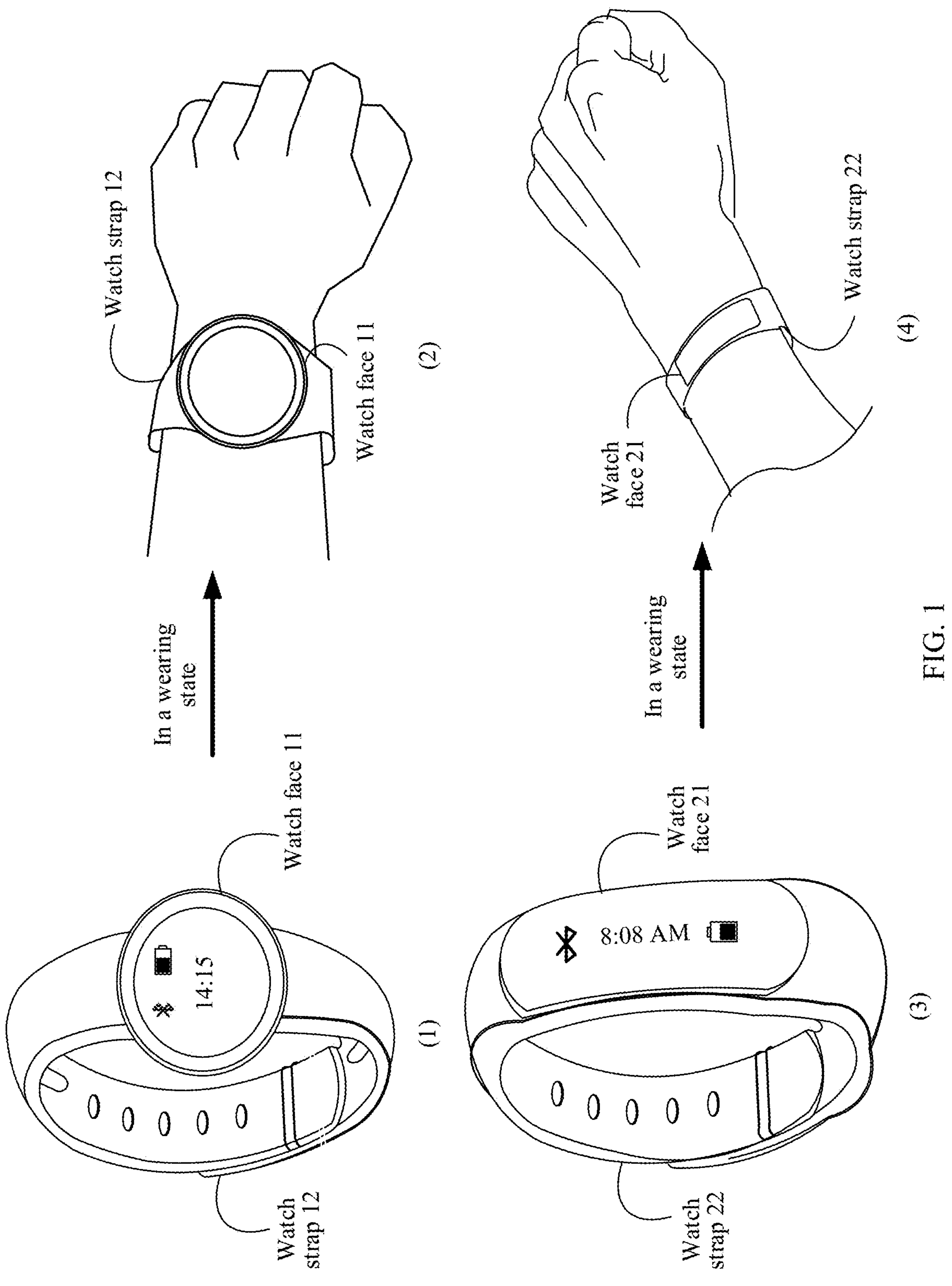
FIG. 1 is an exemplary diagram of an application scenario according to an embodiment of this application.

Referring to FIG. 1, FIG. 1 is a schematic diagram of a smart watch and a smart bracelet in a wearing state.

The smart watch as shown in (1) in FIG. 1 includes a watch face 11 and a watch strap 12. The smart watch in the wearing state is shown in (2) in FIG. 1. A user can wear the smart watch on a wrist through the watch strap 12, so that the back of the watch face 11 can cling to skin. The user can adjust tightness of wearing by adjusting the watch strap 12.

The smart bracelet as shown in (3) in FIG. 1 includes a watch face 21 and a watch strap 22. The smart bracelet in the wearing state is shown in (4) in FIG. 1.

It should be understood that FIG. 1 only schematically describes an application scenario of this application, which does not constitute a limitation on this embodiment of this application, and this application is not limited thereto.

To accurately recognize a heart rhythm type, embodiments of this application provide a heart rhythm detection method and an electronic device. In the embodiments of this application, according to a trajectory of changes in a heart rate difference of a PPG signal with a first preset duration, a parameter (including, but not limited to, an angle, a quantity, an angle standard deviation, and a distance standard deviation) of the trajectory is obtained, and then a heart rhythm type is determined based on the parameter of the trajectory, which can improve accuracy of recognition of a premature beat or atrial fibrillation, prevent recognition of a premature beat signal as an atrial fibrillation signal, and improve user experience.

For convenience of understanding, some terms involved in the embodiments of this application are briefly introduced prior to introduction to the embodiments of this application.

A heart rate refers to a count of heartbeats per minute. A heart rhythm refers to a rhythm of the heartbeats. The heart rhythm may be divided into a normal heart rhythm and an abnormal heart rhythm (or an arrhythmia).

Generally, the normal heart rhythm originates from a sinus node at a frequency of 60 to 100 beats per minute, also known as a sinus rhythm. The arrhythmia occurs when there is an abnormality in any one of a heart rhythm origin site, a cardiac frequency and rhythm, impulse conduction, and the like. According to an expression, the arrhythmia may be represented as bradycardia (e.g., the heart rate is less than 60 beats per minute) or tachycardia (e.g., the heart rate is more than 100 beats per minute).

Exemplarily, the heart rhythm type may have the following situations: a sinus rhythm, a premature beat, bigeminy, trigeminy, atrial fibrillation, ventricular tachycardia, and the like.

The premature beat, also known as premature systole, may occur sporadically or frequently and may irregularly or regularly occur after every normal beat or every few normal beats. The premature beat is a common arrhythmia that may occur in normal people, but is more likely to occur in patients with cardiac neurosis and organic heart diseases.

The bigeminy is a premature systole occurring after every sinus beat. The trigeminy is a premature systole occurring after every two normal beats.

The atrial fibrillation is the most common persistent arrhythmia. The atrial fibrillation has an irregular heartbeat frequency. The atrial fibrillation is a common heart disease.

The ventricular tachycardia is a common arrhythmia with a heartbeat frequency generally exceeding 100 beats.

Figure 2:
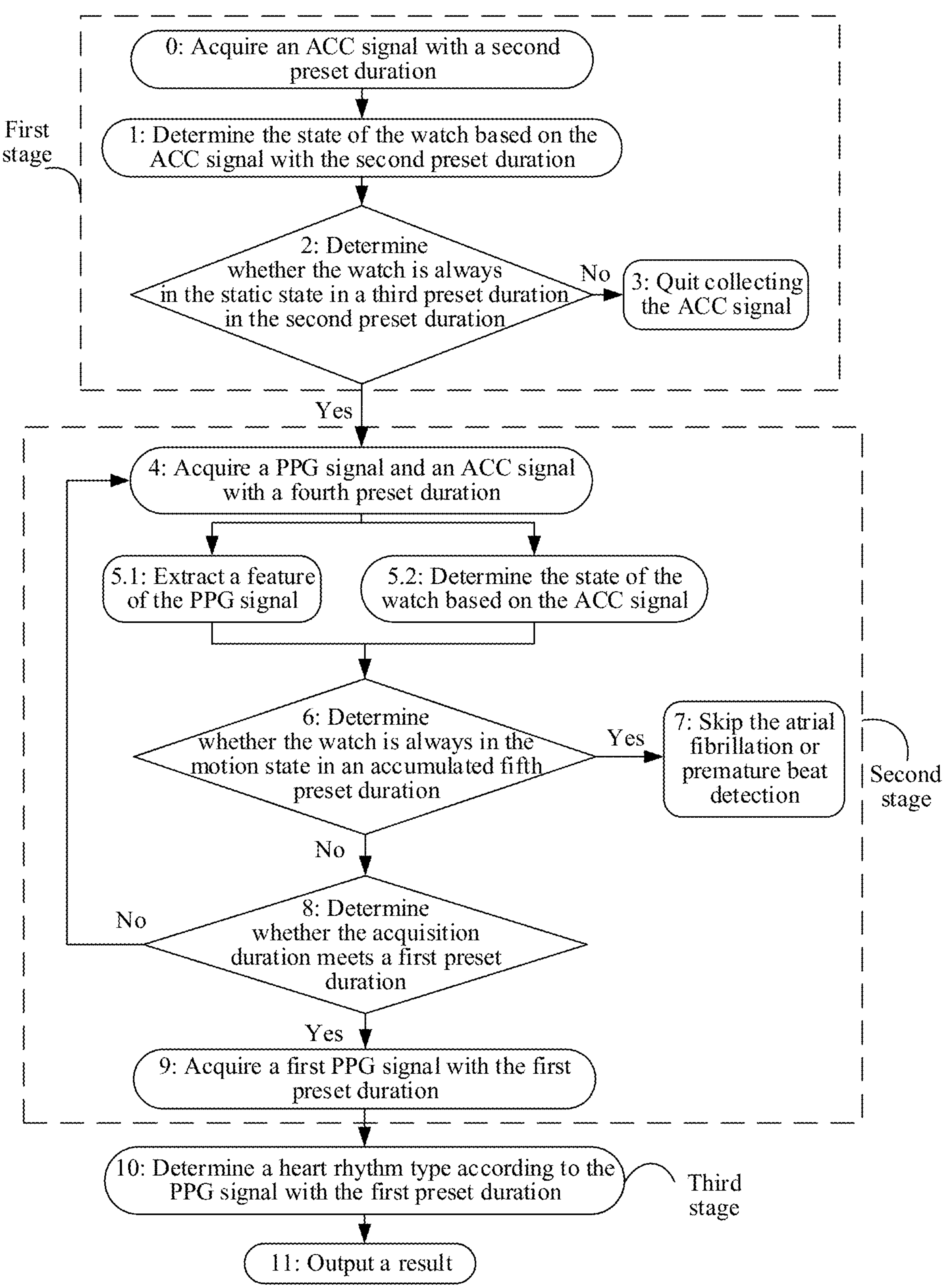
FIG. 2 is a schematic flowchart of a heart rate detection method according to an embodiment of this application.

Referring to FIG. 2, the heart rhythm detection method according to this embodiment of this application is described below with reference to a procedure in FIG. 2. For ease of description, the description is made below by using an example in which the electronic device is a watch.

As shown in FIG. 2, the heart rhythm detection method according to this embodiment of this application may include the following three stages: A first stage is used for determining whether to enter atrial fibrillation or premature beat detection based on an ACC signal. A second stage is used for acquiring a first PPG signal with a first preset duration. A third stage is used for determining a heart rhythm type based on the first PPG signal with the first preset duration.

In a possible implementation, prior to the atrial fibrillation or premature beat detection, the ACC signal can be acquired first to determine the state of the electronic device, so as to determine whether to enter an atrial fibrillation or premature beat detection procedure. It should be understood that the ACC signal is taken as an example for illustration herein, but the embodiments of this application are not limited thereto. In fact, the ACC signal may alternatively be replaced with another information or signal used for determining the state of the electronic device.

Exemplarily, the first stage may be implemented through step 0 to step 3 below.

Step 0: Acquire an ACC signal with a second preset duration.

Optionally, the second preset duration may be formed by n time units (n is an integer greater than or equal to 1).

It should be understood that the embodiments of this application do not specifically limit the type of the time unit. For example, the time unit may be hours, minutes, seconds, microseconds, milliseconds, or other time units. For example, the n time units may be n seconds.

It should also be understood that the ACC signal herein may be actively acquired or passively acquired, which is not specifically limited in the embodiments of this application.

In a possible example, an application may receive an operation of the user (for example, the operation is used for triggering a function of continuously measuring a heart rate). The application includes an atrial fibrillation or premature beat detection function. For example, the application includes, but is not limited to, applications such as heart rate, exercise recording, exercise, and health monitoring. For example, the user clicks on an application in a UI interface to perform heart rate monitoring (such as motion monitoring or continuous measurement in the UI interface), and the ACC signal may be first acquired during the heart rate monitoring, so as to determine, based on the ACC signal, whether to trigger the atrial fibrillation or premature beat detection function.

In a possible example, after receiving the operation of the user, the application may send a trigger action to a system, so that the system invokes an accelerometer (accelerometer) to acquire data (such as the ACC signal) to detect a state of the watch. It should be understood that the accelerometer is taken as an example for illustration herein, but the embodiments of this application are not limited thereto.

Step 1: Determine the state of the watch based on the ACC signal with the second preset duration.

The state of the watch may be a static state or a motion state. The static state refers to a state when the user is wearing the watch and an arm is not swinging. The motion state refers to a state in which the watch is swinging with the arm. For example, the watch is in the motion state when the arm of the user where the watch is worn is drastically swinging.

In a possible implementation, the ACC signal may be 3-axis (generally x-axis, y-axis, and z-axis) data. Optionally, the 3-axis data may be obtained through the accelerometer, and then the state of the watch is calculated every second based on the 3-axis data.

In a possible implementation, the state of the watch may be determined by setting a threshold of motion data (such as an acceleration threshold). For example, an acceleration value of the watch may be calculated through the 3-axis data. If the acceleration value is greater than or equal to the acceleration threshold, it is determined that the watch is in the motion state. If the acceleration value is less than the acceleration threshold, it is determined that the watch is in the static state.

Step 2: Determine whether the watch is always in the static state in a third preset duration in the second preset duration.

If the watch is not always in the static state in the third preset duration, step 3 (quit collecting the ACC signal) is performed, so as to wait for collecting the ACC signal in next cycle or next time. If the watch is always in the static state in the third preset duration, step 4 is performed.

The third preset duration is an accumulated duration. The third preset duration is close to the second preset duration. Exemplarily, when a difference between the second preset duration and the third preset duration is small enough, for example, less than a certain threshold (the threshold may be flexibly selected based on a specific implementation), it may be considered that the two are relatively close.

If the preset duration is expressed in time units, step 2 may alternatively be expressed as: determine (or count) whether the watch is always in the static state in $n_1$ time units accumulated in n time units. A duration formed by the $n_1$ time units is close to a duration formed by the n time units. $n_1$ is less than or equal to n when the two are expressed in a same time unit.

The third preset duration may be formed by the $n_1$ time units. It should be noted that $n_1$ herein is obtained by accumulation. In other words, the $n_1$ time units may be continuous time units or discontinuous time units, which is not specifically limited in the embodiments of this application.

It may be understood that a minimum time unit of the n time units and the $n_1$ time units may be the same or different, which is not specifically limited. For example, the time unit of n is minutes, and the n time units are 1 minute. The time unit of $n_1$ is seconds, and the $n_1$ time units are 58 seconds. In another example, the time units of the two are seconds, the n time units are 60 seconds, and the $n_1$ time units are 58 seconds.

A description is based on an example in which the time unit is seconds. If it is detected that the watch is always in the static state in $n_1$ seconds accumulated in n seconds, atrial fibrillation or premature beat algorithm detection is entered to perform the procedure of the second stage.

Step 2 above may alternatively be expressed in another manner: quit collecting the ACC signal, or stop collecting the ACC signal, and wait for collecting the ACC signal next time or in next cycle before determining the state if it is detected that the watch is in the motion state in n-$n_1$ seconds within n seconds. The n-$n_1$ seconds may be continuous or discontinuous.

After the first stage, if the watch is always in the static state in all the $n_1$ time units, the second stage may be entered to collect a PPG signal. Therefore, continuous acquisition of the PPG signal to detect the heart rhythm type can be prevented, which helps to save power consumption of the electronic device.

Step 3: Quit collecting (or acquiring) the ACC signal.

Exemplarily, the second stage may be implemented through step 4 to step 9 below.

Step 4: Acquire a PPG signal and an ACC signal with a fourth preset duration.

The fourth preset duration may be formed by L1 time units. A description of the time unit may be obtained with reference to the foregoing description. Details are not described herein again. For example, the fourth preset duration is formed by L1 seconds.

Herein, the PPG signal is acquired to provide preparation for subsequent analysis of the heart rhythm type. The ACC signal also needs to be acquired while the PPG signal is acquired. It should be noted that a purpose of acquiring the ACC signal herein is to assist the acquisition of the PPG signal. If it is determined through the ACC signal that the watch has been in the motion state within a fifth preset duration (for example, the arm where the watch is worn continuously drastically swings), the atrial fibrillation or premature beat detection procedure may be quit, or the acquisition of the PPG signal and the ACC signal may be quit.

In a possible implementation, the PPG signal is acquired through a PPG sensor.

In a possible implementation, the AAC signal is acquired through the accelerometer.

Optionally, after the PPG signal with the fourth preset duration is acquired, the PPG signal with the fourth preset duration may be filtered to remove an interference signal (such as interference caused by breathing of the user) or noise, to obtain a filtered PPG signal.

Optionally, the filtering includes low-pass filtering and high-pass filtering.

Step 5.1: Extract a feature (such as a peak) of the PPG signal.

For example, the peak may be extracted based on the filtered PPG signal.

Step 5.2: Determine the state of the watch based on the ACC signal.

The step of determining the state of the watch herein is similar to step 1 above. Refer to the related description above. Details are not described herein again.

Step 6: Determine whether the watch is always in the motion state in an accumulated fifth preset duration.

Step 7 is performed if the watch is always in the motion state in the accumulated fifth preset duration. Step 8 is performed if the watch is not always in the motion state in the accumulated fifth preset duration.

The fifth preset duration is formed by L2 time units. The fifth preset duration is greater than the first preset duration. The fifth preset duration is greater than the second preset duration.

A description of the time unit may be obtained with reference to the foregoing description. Details are not described herein again. For example, the time unit is seconds. If the watch has been in the motion state for an accumulated duration of L2 seconds, step 7 (skip the atrial fibrillation or premature beat detection) is performed. If not, the PPG signal and the ACC signal with the fourth preset duration are acquired until an acquisition duration meets the first preset duration, and step 8 is performed. Optionally, the L2 seconds may be greater than the n-$n_1$ seconds in step 2.

Step 7: Skip the atrial fibrillation or premature beat detection.

Skipping the atrial fibrillation or premature beat detection procedure means stopping collecting the PPG signal and the ACC signal and waiting for next judgment of the ACC signal.

Step 8: Determine whether the acquisition duration meets a first preset duration.

The first preset duration refers to an accumulated duration during which the PPG signal is acquired when it is determined that the watch is not always in the motion state within the fifth preset duration. The first preset duration is greater than the fourth preset duration. For example, the first preset duration is 1 minute, and the fourth preset duration is 10 seconds.

If the acquisition duration meets the first preset duration, acquiring the PPG signal and the ACC signal is stopped, and step 9 is performed. If the acquisition duration does not meet the first preset duration, the method goes back to continue step 4.

Step 9: Acquire a first PPG signal with the first preset duration.

The first preset duration may be formed by L3 time units. A description of the time unit may be obtained with reference to the foregoing description. Details are not described herein again.

Specifically, when the acquisition duration meets the first preset duration, features of a plurality of PPG signals with the fourth preset duration are spliced together in chronological order (or sorted in chronological order) to obtain the first PPG signal with the first preset duration. For example, the first preset duration is 1 minute, and the fourth preset duration is 6 seconds.

Herein, splicing features of the first PPG signal with the first preset duration together means: combining the plurality of PPG signals with the fourth preset duration together. In other words, the first PPG signal with the first preset duration is formed by a plurality of PPG signals, and a duration of each PPG signal is the fourth preset duration. Optionally, each PPG signal may be a filtered PPG signal. Alternatively, each PPG signal may be an unfiltered PPG signal, and the plurality of PPG signals are spliced together and then uniformly filtered, which is not limited in the embodiments of this application.

It should be noted that the first PPG signal with the first preset duration herein does not include the PPG signal acquired when the atrial fibrillation or premature beat detection (continuously in the motion state in the fifth preset duration) is skipped.

Through the second stage, an active PPG signal can be obtained, thereby providing preparation for subsequent detection of a heart rhythm type.

Based on the above, the first PPG signal with the first preset duration can be obtained through the first stage and the second stage above. Then, the third stage may be entered, that is, the heart rhythm type is determined according to the first PPG signal with the first preset duration.

It should be understood that the first stage and the second stage above may be optional steps, which are not specifically limited in the embodiments of this application.

The third stage: Step 10: Determine a heart rhythm type according to the first PPG signal with the first preset duration.

The heart rhythm type includes: a premature beat, atrial fibrillation, a sinus rhythm, ventricular tachycardia, bigeminy, trigeminy, and the like.

How to determine the heart rhythm type based on the first PPG signal with the first preset duration may be described in detail later with reference to FIG. 3.

Step 11: Output a result.

The result outputted in step 11 is the heart rhythm type obtained through step 10.

It may be understood that the result may be displayed in a form on a display screen of a mobile phone, a watch, or a bracelet.

In a possible implementation, the heart rhythm type is displayed. For example, in an interface shown in (2) in FIG. 11A, a count of abnormal heart rhythms may be displayed in the watch.

In a possible implementation, the user may view a heart rhythm result on a terminal connected to the watch or bracelet. For example, in an interface shown in (3) in FIG. 11B, the user may view a count of abnormal heart rhythms in statistical details in an APP.

Optionally, another procedure may also be included in FIG. 2. For example, before step 0, it may alternatively be first determined whether a wearer of the watch is a living body or detected whether the watch is worn by the user. For example, whether the wearer of the watch is a living body can be detected in combination with an infrared detection technology and a living body wearing algorithm. In a case that the user wears the watch, there may be a need for heart rate monitoring, thereby analyzing the heart rhythm type.

It should be understood that the procedure in FIG. 2 is merely an exemplary description, and does not constitute a limitation on this embodiment of this application.

Figure 3:
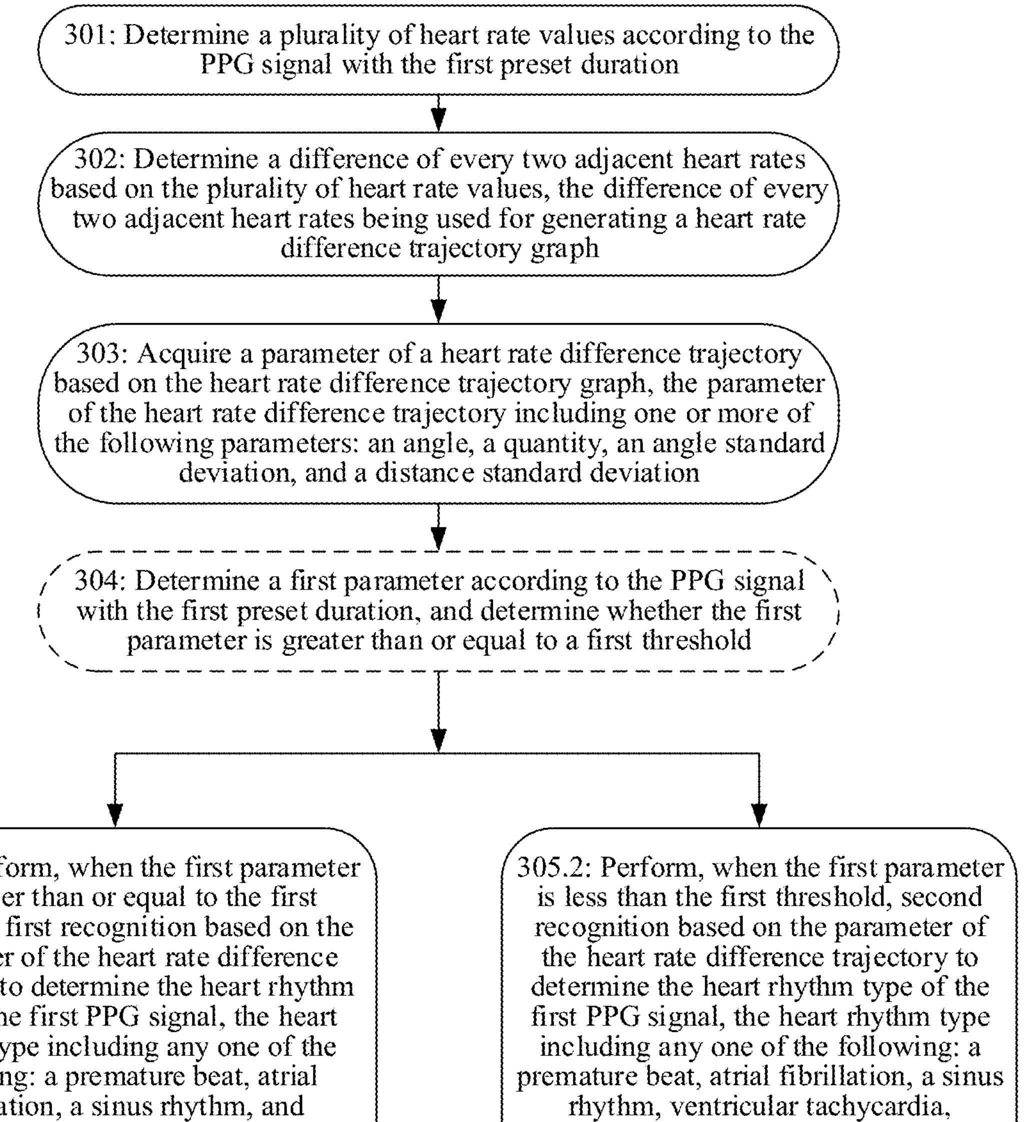
FIG. 3 is a schematic flowchart of a method for determining a heart rhythm type according to an embodiment of this application.

Referring to FIG. 3, a specific process of the third stage is described in detail below with reference to FIG. 3.

FIG. 3 is a schematic flowchart of a method for determining a heart rhythm type according to an embodiment of this application. It should be understood that the method in FIG. 3 may be used in combination with the procedure in FIG. 2 or used alone, which is not specifically limited in the embodiments of this application. As shown in FIG. 3, the method includes the following steps:

Step 301: Determine a plurality of heart rate (heart rate, HR) values according to the first PPG signal with the first preset duration.

As can be seen from the above, the first PPG signal with the first preset duration may be formed by a plurality of PPG signals, and a duration of each PPG signal is the fourth preset duration. Correspondingly, the plurality of heart rate values herein are: heart rate values determined based on the plurality of PPG signals. For example, assuming that the first preset duration is 1 minute and the fourth preset duration is 10 seconds, the plurality of heart rate values refer to: a plurality of heart rate values obtained from a PPG signal formed by a first 10-second PPG signal, a second 10-second PPG signal, . . . , and a sixth 10-second PPG signal.

In an implementation, a pulse interval (R-R interval, RRI) is extracted based on a peak of the first PPG signal with the first preset duration, and then a heart rate is calculated according to each RRI. The RRI refers to a time interval between two adjacent peaks. The RRI may be understood as an interval between two R waves. An R wave is a concept of electrocardiography, which refers to a wave with an upward electrocardiographic trend, and may alternatively be understood as a wave including a peak.

Exemplarily, the heart rate may be calculated by using the following formula:

$$HR = \frac{60}{RRI}$$

where HR denotes a heart rate value, and RRI denotes an interval.

It should be understood that the manner of calculating the heart rate herein is only an example description, but the embodiments of this application are not limited thereto. There may alternatively be other manners of calculating the heart rate.

Step 302: Determine a difference of every two adjacent heart rates based on the plurality of heart rate values, the difference of every two adjacent heart rates being used for generating a heart rate difference trajectory graph.

A heart rate difference may be expressed as ΔHR. It may be understood that the heart rate difference may be positive or negative.

In this embodiment of this application, the heart rate difference trajectory graph is drawn by using a plurality of heart rate differences and a heart rate difference threshold, to achieve a purpose of analyzing a type of an arrhythmia.

Optionally, the heart rate difference threshold may be a priori value. For example, the heart rate difference threshold is set to 6 or −6.

The heart rate difference trajectory graph is a scatter plot, which reflects distribution characteristics of the trajectory formed by the heart rate differences. For example, a Poincaré plot (Poincaré plot) is used as the heart rate difference trajectory graph.

In an implementation, the Poincaré plot is generated by using heart rate differences. For example, if n+1 heart rate differences ($\Delta HR_1$, . . . , and $\Delta HR_{n+1}$ respectively) are obtained, the Poincaré plot is drawn by using the n+1 heart rate differences. The Poincaré plot is drawn with $\Delta HR_n$ as an ordinate and $\Delta HR_{n+1}$ as an abscissa. With the origin as a center, the origin divides the Poincaré plot into 9 regions respectively in four directions of up, down, left, and right by taking a heart rate difference as a boundary. The regions are respectively labeled as: a region 0, a region 1, a region 2, a region 3, . . . , and a region 8. A description will be made below with reference to specific drawings.

Step 303: Acquire a parameter of a heart rate difference trajectory based on the heart rate difference trajectory graph, the parameter of the heart rate difference trajectory including one or more of the following parameters: an angle, a quantity, an angle standard deviation, and a distance standard deviation.

Specifically, after the heart rate difference trajectory graph is obtained, related parameters of the heart rate difference trajectories in the graph may be calculated, including, but not limited to, the following parameters: angles of the trajectories, a quantity of the trajectories falling in the corresponding regions, an angle standard deviation of the trajectories, and a distance standard deviation of the trajectories.

The heart rate difference trajectory graph includes a plurality of different trajectory types. The heart rate difference trajectories may be represented by numbers of the regions of the Poincaré plot.

In a possible implementation, a heart rate difference trajectory may be expressed as a triangle formed by a heart rate difference falling in a region A, a heart rate difference falling in a region B, and a heart rate difference falling in a region C. For example, the trajectory is expressed as A-B-C. The regions referred to herein may specifically be the regions into which the Poincaré plot is divided as referred to above.

An angle of the heart rate difference trajectory refers to an angle in the above triangle. An apex of the angle is the heart rate difference falling in the region B.

A trajectory 1-2-3 is taken as an example for illustration (explanation of other subsequent trajectories may be understood with reference to the description herein), and the trajectory 1-2-3 indicates that a connecting line of the heart rate differences passes through the region 1, the region 2, and the region 3. For example, a trajectory obtained by connecting a heart rate difference a falling in the region 1 with a heart rate difference b falling in the region 2 and then connecting the heart rate difference b falling in the region 2 with a heart rate difference c falling in the region 3 is the trajectory 1-2-3. The heart rate difference a, the heart rate difference b, and the heart rate difference c are sorted in chronological order.

An angle of the trajectory 1-2-3 is expressed as $\theta_{123}$. $\theta_{123}$ denotes an angle of ∠123, and ∠123 denotes an angle with the heart rate difference falling in the region 2 as an apex.

A quantity of the heart rate difference trajectory refers to a quantity of heart rate differences falling in the corresponding regions. For example, a quantity of the trajectory A-B-C refers to: a quantity of heart rate differences falling near the region A and the region C. In another example, the quantity of the trajectory A-B-C refers to: a quantity of heart rate differences falling near the region A, the region B, and the region C.

For example, a quantity of the trajectory 1-2-3 may be expressed as $num_{123}$. $num_{123}$ denotes a quantity of heart rate differences falling near the region 1 and the region 3.

An angle standard deviation of the heart rate difference refers to a standard deviation of angles. The standard deviation of angles is calculated based on an average value and a standard value of the angles. A calculation manner of the standard deviation may be obtained with reference to the existing description.

For example, the angle standard deviation of the above trajectory 1-2-3 is expressed as $sd_{123}$. $sd_{123}$ may be calculated by using the following formula:

$$sd_{123} = \sqrt{\frac{\sum_{i=1}^{n}(x_i - \overline{x})^2}{n-1}}$$

where $\overline{x}$ denotes a mean of a sequence $x_1, x_2, \ldots, x_n$. It may be understood that x is substituted into a value of an angle in the above formula if the angle standard deviation is calculated. x is substituted into a value of a distance in the above formula if the distance standard deviation is calculated.

In a possible implementation, the heart rate difference trajectory may alternatively be expressed as a connecting line between a heart rate difference falling in a region E and a heart rate difference falling in a region F, that is, a straight line E-F.

In a case that the heart rate difference trajectory is a straight line, the angle of the heart rate difference trajectory may be understood as a corresponding angle when the straight line E-F is used as a slope.

In a case that the heart rate difference trajectory is a straight line, the distance standard deviation of the heart rate difference trajectory refers to: a standard deviation of a distance from an origin (0,0) to the straight line.

For example, $sd\_d_{24}$ denotes a standard deviation of a distance from the origin to a straight line 2-4.

Exemplarily, the heart rate difference trajectory may have the following situations: a first trajectory (1-2-3), a second trajectory (6-4-5), a third trajectory (1-0-3), a fourth trajectory (6-0-5), a fifth trajectory (2-4), a sixth trajectory (4-2), a parameter of a seventh trajectory (1-2), an eighth trajectory (2-3), a ninth trajectory (6-4), and a tenth trajectory (4-5).

Exemplarily, an angle parameter of the first trajectory is expressed as $\theta_{123}$. An angle parameter of the second trajectory is expressed as $\theta_{645}$. An angle parameter of the third trajectory is expressed as $\theta_{103}$. An angle parameter of the fourth trajectory is expressed as $\theta_{605}$. An angle parameter of the fifth trajectory is expressed as $\theta_{24}$. An angle parameter of the sixth trajectory is expressed as $\theta_{42}$. An angle parameter of the seventh trajectory is expressed as $\theta_{12}$. An angle parameter of the eighth trajectory is expressed as $\theta_{23}$. An angle parameter of the ninth trajectory is expressed as $\theta_{64}$. An angle parameter of the tenth trajectory is expressed as $\theta_{45}$.

Exemplarily, a quantity parameter of the first trajectory is expressed as $num_{123}$. A quantity parameter of the second trajectory is expressed as $num_{645}$. A quantity parameter of the third trajectory is expressed as $num_{103}$. A quantity parameter of the fourth trajectory is expressed as $num_{605}$. A quantity parameter of the fifth trajectory is expressed as $num_{24}$. A quantity parameter of the sixth trajectory is expressed as $num_{42}$. A quantity parameter of the seventh trajectory is expressed as $num_{12}$. A quantity parameter of the eighth trajectory is expressed as $num_{23}$. A quantity parameter of the ninth trajectory is expressed as $num_{64}$. A quantity parameter of the tenth trajectory is expressed as $num_{45}$.

Exemplarily, an angle standard deviation parameter of the first trajectory is expressed as $sd_{123}$. An angle standard deviation parameter of the second trajectory is expressed as $sd_{645}$. An angle standard deviation parameter of the third trajectory is expressed as $sd_{103}$. An angle standard deviation parameter of the fourth trajectory is expressed as $sd_{605}$. An angle standard deviation parameter of the fifth trajectory is expressed as $sd_{24}$. An angle standard deviation parameter of the sixth trajectory is expressed as $sd_{42}$. An angle standard deviation parameter of the seventh trajectory is expressed as $sd_{12}$. An angle standard deviation parameter of the eighth trajectory is expressed as $sd_{23}$. An angle standard deviation parameter of the ninth trajectory is expressed as $sd_{64}$. An angle standard deviation parameter of the tenth trajectory is expressed as $sd_{45}$.

Exemplarily, a standard deviation parameter of a distance from the origin (0,0) to the fifth trajectory (2-4) is expressed as $sd\_d_{24}$. A standard deviation parameter of a distance from the origin (0,0) to the sixth trajectory (4-2) is expressed as $sd\_d_{42}$.

Optionally, the parameter of the heart rate difference trajectory further includes a first probability parameter and a first quantity. The first probability parameter refers to a parameter of a probability of falling in the region 0. For example, the first probability parameter is expressed as $r_{zero}$. The first quantity refers to a quantity falling outside the region 0. For example, the first quantity is expressed as $num_{outside}$.

It should be noted that heart rate difference trajectories of different heart rhythm types have different characteristics, or have respective laws. In this embodiment of this application, in combination with the above parameters of the heart rate difference trajectories, it can be determined which type of heart rhythm the PPG signal with the first preset duration belongs to.

Optionally, step 304: Determine a first parameter according to the first PPG signal with the first preset duration, and determine whether the first parameter is greater than or equal to a first threshold.

Herein, comparison of a size relationship between the first parameter and the first threshold is to perform preliminary recognition of atrial fibrillation. If the first parameter is greater than or equal to the first threshold, a probability of atrial fibrillation is greater than a probability of non-atrial fibrillation in this case, and then an atrial fibrillation recognition window is entered. If the first parameter is less than the first threshold, the probability of atrial fibrillation is less than the probability of non-atrial fibrillation in this case, and then a non-atrial fibrillation recognition window is entered. In this way, a data flow can be split to save a subsequent judgment procedure, thereby saving power consumption of the electronic device. For example, in a case of a non-atrial fibrillation recognition window, a procedure of determining whether the bigeminy or trigeminy occurs may be involved in the following, while a judgment procedure in an atrial fibrillation recognition window may not be involved.

Certainly, even if the atrial fibrillation recognition window is entered, it does not mean that the heart rhythm type has to be the atrial fibrillation, and further judgment needs to be made in combination with the parameter of the heart rate difference trajectory to determine the heart rhythm type. Similarly, even if the non-atrial fibrillation recognition window is entered, it does not mean that the heart rhythm type has to be the non-atrial fibrillation, and further judgment needs to be made in combination with the parameter of the heart rate difference trajectory to determine the heart rhythm type, thereby improving accuracy.

Optionally, the determining a first parameter according to the PPG signal with the first preset duration includes: extracting a plurality of RRIs according to a peak of the PPG signal with the first preset duration; and calculating a difference between every two adjacent RRIs according to the plurality of RRIs, the difference between every two adjacent RRIs being used for determining the first parameter.

For ease of description, the difference between every two adjacent RRIs (an RRI difference for short) may be expressed as ΔRRI.

For example, a root mean square and a sample entropy may be calculated based on a plurality of ΔRRI, and then the first parameter is determined based on the root mean square and the sample entropy.

In a possible implementation, the first parameter is calculated by using the following formula:

$$\text{Comb} = w \times \text{RMSSD} + (1 - w) \times \text{SampEn}$$

where Comb denotes the first parameter, w denotes a weight value, RMSSD denotes a root mean square of the RRI differences, and SampEn denotes a sample entropy of RRIs. $0 \le w \le 1$. Generally, a value of RMSSD is greater than SampEn. Therefore, a weight of RMSSD is less than that of SampEn.

where N denotes a quantity of ΔRRI, and ΔRRI denotes a difference between adjacent RRIs.

The sample entropy is a metric used for measuring complexity of an RRI sequence. The sample entropy measures the complexity of the RRI sequence by measuring a probability that the RRI sequence generates a new pattern. The greater the probability of generation of the new pattern, the greater the complexity of the sequence.

Exemplarily, in Matlab, the sample entropy may be calculated by invoking a SampEn function. An example of a Matlab code is as follows:

```
function SampEnVal=SampEn(data,m,r)
```

It may be understood that the definition of the above SampEn function can be defined based on a specific implementation, which is not specifically limited in the embodiments of this application.

It should be understood that the above descriptions about the root mean square and the sample entropy are only exemplary descriptions, and the embodiments of this application are not limited thereto.

It may be understood that step 304 may be an optional step. As a possible implementation, step 304 may alternatively not be needed. That is, the heart rhythm type of the first PPG signal is determined by using the parameter of the heart rate difference trajectory.

Step 305.1: Perform, when the first parameter is greater than or equal to the first threshold, first recognition (or enter an atrial fibrillation label window for recognition) based on the parameter of the heart rate difference trajectory to determine the heart rhythm type of the first PPG signal, the heart rhythm type including any one of the following: a premature beat, atrial fibrillation, a sinus rhythm, and ventricular tachycardia.

In other words, in a case of entering the atrial fibrillation label window for recognition, it may be determined whether parameters of different trajectories meet a corresponding preset condition (e.g., determine a relationship between the parameters and a corresponding threshold), so as to recognize the heart rhythm type.

Various implementations for the first recognition are described below.

In a possible implementation, the heart rhythm type is the premature beat when a parameter of the first trajectory (1-2-3) and a parameter of the second trajectory (6-4-5) meet a first preset condition.

Optionally, that a parameter of the first trajectory (1-2-3) and a parameter of the second trajectory (6-4-5) meet a first preset condition includes: a sum of a quantity parameter of the first trajectory and a quantity parameter of the second trajectory being greater than or equal to a first quantity threshold, and an angle standard deviation parameter of the first trajectory and an angle standard deviation parameter of the second trajectory being both less than or equal to a first angle standard deviation threshold.

For example, when $(num_{123}+num_{645}) \geq Th\_num1$ and both $sd_{123}$ and $sd_{645}$ are less than or equal to a threshold Th_sd1, it is a premature beat signal.

Figure 4:
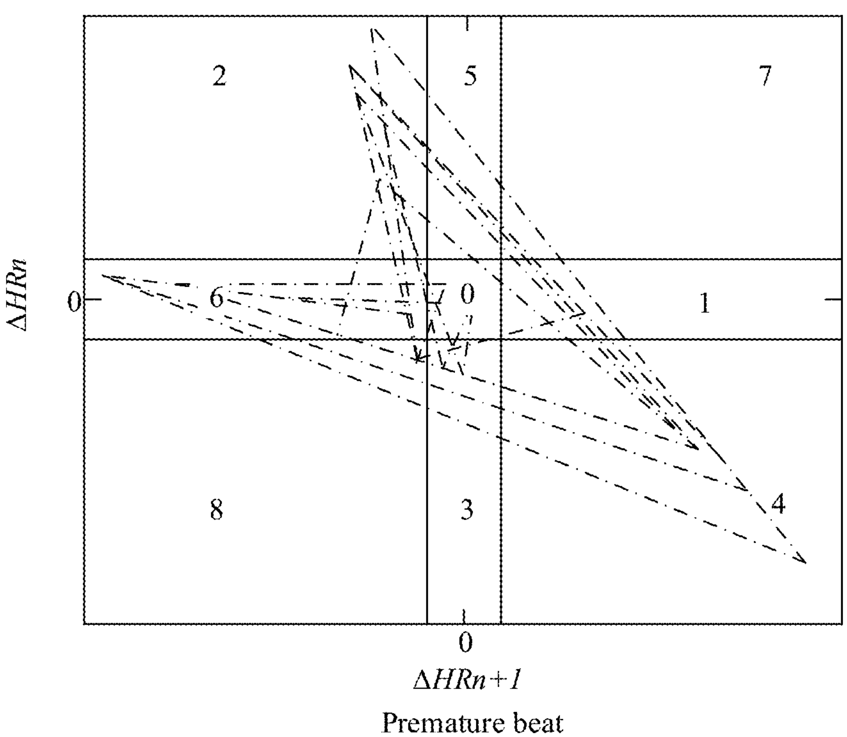
FIG. 4 is a schematic diagram of a heart rate difference trajectory of a premature beat according to an embodiment of this application.

FIG. 4 is a schematic diagram of a heart rate difference trajectory of a premature beat. As shown in FIG. 4, in FIG. 4, the Poincaré plot is drawn with $\Delta HR_n$ as an ordinate and $\Delta HR_{n+1}$ as an abscissa. With the origin as a center, the origin divides the Poincaré plot into 9 regions respectively in four directions of up, down, left, and right by taking a heart rate difference as a boundary. The regions are respectively: a region 0, a region 1, a region 2, . . . , and a region 8. It should be understood that a drawing principle of FIG. 5 to FIG. 10 below is similar to that of FIG. 4, which may be obtained with reference to the description herein. Details are not described below again.

As can be seen from FIG. 4, the trajectory of the premature beat is like a triangle with overlapping. The premature beat is recognized according to $sd_{123}$, $sd_{645}$, $num_{123}$, and $num_{645}$.

In a possible implementation, the heart rhythm type is the atrial fibrillation when the parameter of the first trajectory (1-2-3) and the parameter of the second trajectory (6-4-5) meet a second preset condition and a first probability parameter meets a third preset condition.

Optionally, that the parameter of the first trajectory (1-2-3) and the parameter of the second trajectory (6-4-5) meet a second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold.

Optionally, that a first probability parameter meets a third preset condition includes: the first probability parameter being less than a first probability threshold.

For example, when $(num_{123}+num_{645}) \geq Th\_num1$, at least one of $sd_{123}$ and $sd_{645}$ is greater than the threshold Th_sd1, and $r_{zero}<Th\_r1$, it is the atrial fibrillation.

Figure 5:
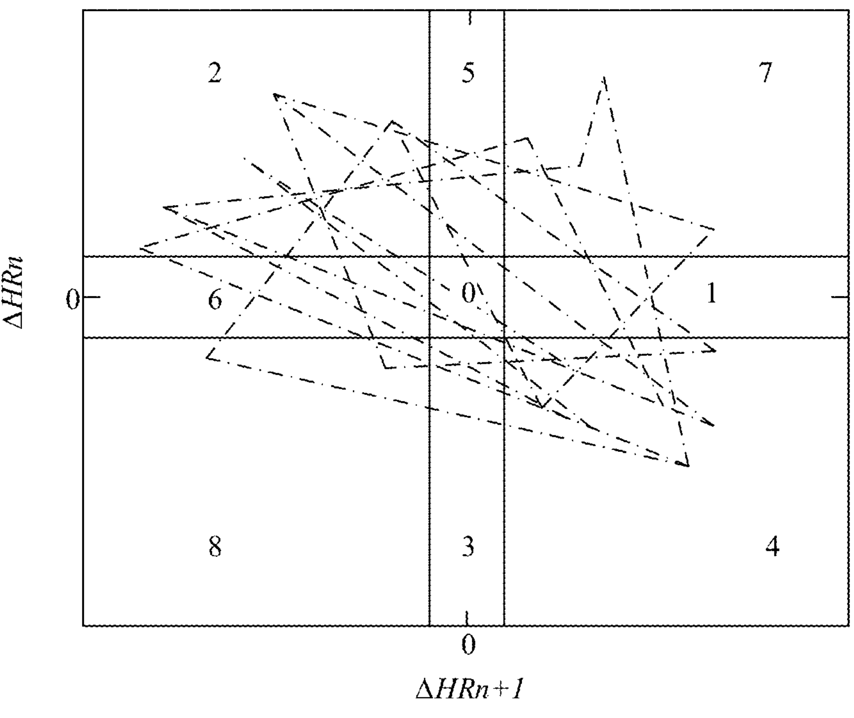
FIG. 5 is a schematic diagram of a heart rate difference trajectory of normal atrial fibrillation according to an embodiment of this application.
Figures 6, 7:
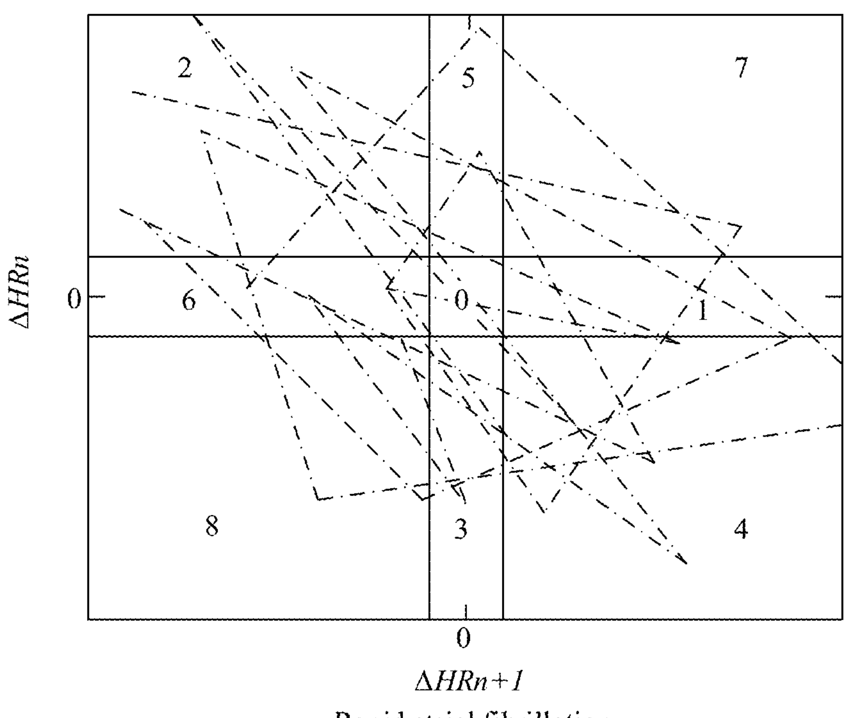
FIG. 6 is a schematic diagram of a heart rate difference trajectory of rapid atrial fibrillation according to an embodiment of this application.
FIG. 7 is a schematic diagram of a heart rate difference trajectory of a sinus rhythm according to an embodiment of this application.

FIG. 5 is a schematic diagram of a heart rate difference trajectory of a normal atrial fibrillation. FIG. 6 is a schematic trajectory diagram of a heart rate difference trajectory of rapid atrial fibrillation.

FIG. 5 and FIG. 6 above are both schematic diagrams of a heart rate difference trajectory of atrial fibrillation. As can be seen from FIG. 5 and FIG. 6, the trajectory of the atrial fibrillation is relatively random and disordered, and rarely overlaps, so $sd_{123}$ and $sd_{645}$ are relatively large.

In a possible implementation, the heart rhythm type is the sinus rhythm when the parameter of the first trajectory (1-2-3) and the parameter of the second trajectory (6-4-5) meet the second preset condition and the first probability parameter does not meet the third preset condition.

Optionally, that the parameter of the first trajectory (1-2-3) and the parameter of the second trajectory (6-4-5) meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold.

Optionally, that the first probability parameter does not meet the third preset condition includes: the first probability parameter being no less than the first probability threshold, or the first probability parameter being greater than or equal to the first probability threshold.

For example, when $(num_{123}+num_{645}) \geq Th\_num1$, it is the sinus rhythm if at least one of $sd_{123}$ and $sd_{645}$ is greater than the threshold Th_sd1 and $r_{zero}$ is greater than or equal to Th_r1.

FIG. 7 is a schematic diagram of a heart rate difference trajectory of a sinus rhythm. As can be seen from FIG. 7, points of the sinus rhythm are mainly concentrated in the region 0. The sinus rhythm may be recognized according to $r_{zero}$. In addition, the sinus rhythm may alternatively be recognized according to $num_{outside}$. For example, in an implementation of second recognition below, a related implementation of the sinus rhythm may be recognized according to $num_{outside}$. A related constraint will be described in detail later.

In a possible implementation, when the parameter of the first trajectory (1-2-3) and the parameter of the second trajectory (6-4-5) meet a fourth preset condition and the parameter of the first trajectory (1-2-3) and a parameter of the third trajectory (1-0-3) meet a fifth preset condition; or when the parameter of the first trajectory (1-2-3) and the parameter of the second trajectory (6-4-5) meet a fourth preset condition and the parameter of the second trajectory (6-4-5) and a parameter of the fourth trajectory (6-0-5) meet a sixth preset condition, the heart rhythm type is the ventricular tachycardia.

Optionally, that the parameter of the first trajectory (1-2-3) and the parameter of the second trajectory (6-4-5) meet a fourth preset condition includes: the sum of the quantity parameter of the first trajectory and the quantity parameter of the second trajectory being less than the first quantity threshold.

Optionally, that the parameter of the first trajectory (1-2-3) and a parameter of the third trajectory (1-0-3) meet a fifth preset condition includes: a sum of the quantity parameter of the first trajectory and a quantity parameter of the third trajectory being greater than or equal to a second quantity threshold, the angle standard deviation parameter of the first trajectory and an angle standard deviation parameter of the third trajectory being both less than or equal to a second angle standard deviation threshold, and an angle mean parameter of the first trajectory being less than that of the third trajectory.

Optionally, that the parameter of the second trajectory (6-4-5) and a parameter of the fourth trajectory (6-0-5) meet a sixth preset condition includes: a sum of the quantity parameter of the second trajectory and the quantity parameter of the third trajectory being greater than or equal to the second quantity threshold, the angle standard deviation parameter of the second trajectory and the angle standard deviation parameter of the third trajectory being both less than or equal to the second angle standard deviation threshold, and an angle mean parameter of the second trajectory being less than that of the fourth trajectory.

For example, when $(num_{123}+num_{645})<Th\_num1$, when $(num_{123}+num_{103})\geq Th\_num2$, both $sd_{123}$ and $sd_{103}$ are less than or equal to the threshold Th_sd2, and $mean\theta_{123}<mean\theta_{103}$, or when $(num_{645}+num_{605})\geq Th\_num2$, both $sd_{645}$ and $sd_{605}$ are less than or equal to the threshold Th_sd2, and $mean\theta_{645}<mean\theta_{605}$, it is the ventricular tachycardia. Mean denotes averaging.

Figure 8:
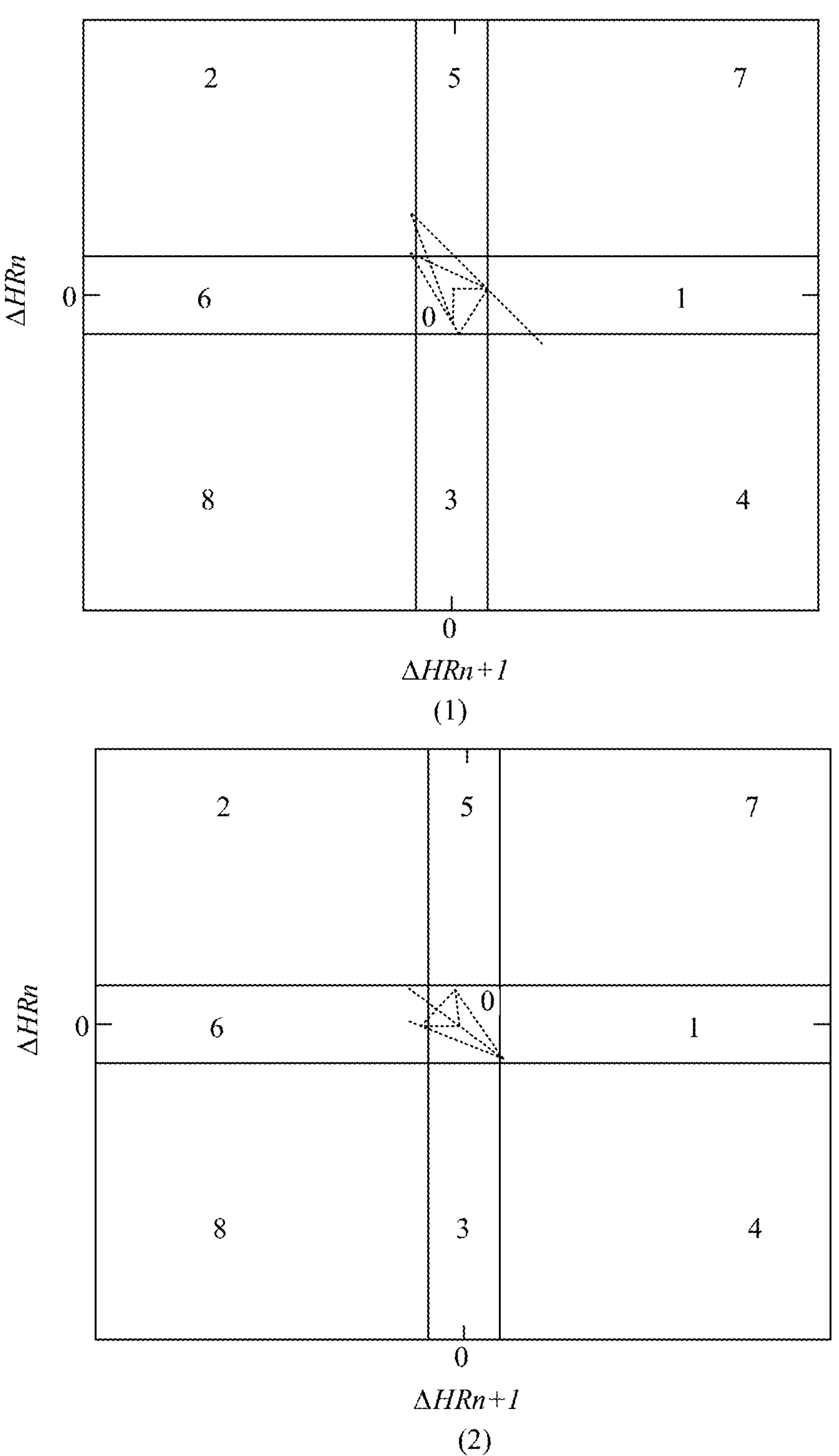
FIG. 8 is a schematic diagram of a heart rate difference trajectory of ventricular tachycardia according to an embodiment of this application.

FIG. 8 is a schematic diagram of a heart rate difference trajectory of ventricular tachycardia. As can be seen from (1) in FIG. 8, trajectories of the ventricular tachycardia centered on '1-2-3' and '1-0-3'. The ventricular tachycardia may be recognized according to $\theta_{123}$, $\theta_{103}$, $num_{123}$, $num_{103}$, $sd_{123}$, and $sd_{103}$. As can be seen from (2) in FIG. 8, trajectories of the ventricular tachycardia centered on '6-4-5' and '6-0-5'. The ventricular tachycardia may be recognized according to $\theta_{645}$, $\theta_{605}$, $num_{645}$, $num_{605}$, $sd_{645}$, and $sd_{605}$.

In a possible implementation, the heart rhythm type is the atrial fibrillation when the parameter of the first trajectory (1-2-3) and the parameter of the second trajectory (6-4-5) meet the fourth preset condition and the first probability parameter meets a seventh preset condition.

Optionally, that the parameter of the first trajectory (1-2-3) and the parameter of the second trajectory (6-4-5) meet the fourth preset condition includes: the sum of the quantity parameter of the first trajectory and the quantity parameter of the second trajectory being less than the first quantity threshold.

Optionally, that the first probability parameter meets a seventh preset condition includes: the first probability parameter being less than a second probability threshold.

For example, when $(num_{123}+num_{645})<Th\_num1$ and $r_{zero}<Th\_r2$, it is the atrial fibrillation.

In a possible implementation, the heart rhythm type is the sinus rhythm when the parameter of the first trajectory (1-2-3) and the parameter of the second trajectory (6-4-5) meet the fourth preset condition and the first probability parameter does not meet the seventh preset condition.

Optionally, that the parameter of the first trajectory (1-2-3) and the parameter of the second trajectory (6-4-5) meet the fourth preset condition includes: the sum of the quantity parameter of the first trajectory and the quantity parameter of the second trajectory being less than the first quantity threshold.

Optionally, that the first probability parameter does not meet the seventh preset condition includes: the first probability parameter being no less than the second probability threshold, or the first probability parameter being greater than or equal to the second probability threshold.

For example, when $(num_{123}+num_{645})<Th\_num1$ and $r_{zero}\geq Th\_r2$, it is the sinus rhythm.

Step 305.2: Perform, when the first parameter is less than the first threshold, second recognition (or enter a non-atrial fibrillation label window for recognition) based on the parameter of the heart rate difference trajectory to determine the heart rhythm type of the first PPG signal, the heart rhythm type including any one of the following: a premature beat, atrial fibrillation, a sinus rhythm, ventricular tachycardia, bigeminy, and trigeminy.

In other words, in a case of entering the non-atrial fibrillation label window for recognition, it may be determined whether parameters of different trajectories meet a corresponding preset condition (e.g., determine a relationship between the parameters and a corresponding threshold), so as to recognize the heart rhythm type.

Various implementations for the second recognition are described below.

In a possible implementation, the heart rhythm type is the premature beat when the parameter of the first trajectory (1-2-3) and the parameter of the second trajectory (6-4-5) meet the first preset condition.

Optionally, that the parameter of the first trajectory (1-2-3) and the parameter of the second trajectory (6-4-5) meet the first preset condition includes: the sum of the quantity parameter of the first trajectory and the quantity parameter of the second trajectory being greater than or equal to the first quantity threshold, and the angle standard deviation parameter of the first trajectory and the angle standard deviation parameter of the second trajectory being both less than or equal to the first angle standard deviation threshold.

For example, when $(num_{123}+num_{645})\geq Th\_num1$, it is a premature beat signal if both $sd_{123}$ and $sd_{645}$ are less than or equal to the threshold Th_sd1.

In a possible implementation, the heart rhythm type is the atrial fibrillation when the parameter of the first trajectory (1-2-3) and the parameter of the second trajectory (6-4-5) meet the second preset condition.

Optionally, that the parameter of the first trajectory (1-2-3) and the parameter of the second trajectory (6-4-5) meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold.

For example, when $(num_{123}+num_{645})\geq Th\_num1$ and at least one of $sd_{123}$ and $sd_{645}$ is greater than the threshold Th_sd1, it is the atrial fibrillation. As can be seen, when $(num_{123}+num_{645})\geq Th\_num1$, a difference between a condition for determining the atrial fibrillation herein and a condition for determining the atrial fibrillation in step 305.1 is that: there is no need herein to make judgment in combination with the first probability parameter.

In a possible implementation, when the parameter of the first trajectory (1-2-3) and the parameter of the second trajectory (6-4-5) meet the fourth preset condition and the parameter of the first trajectory (1-2-3) and the parameter of the third trajectory (103) meet the fifth preset condition; or when the parameter of the first trajectory (1-2-3) and the parameter of the second trajectory (6-4-5) meet the fourth preset condition and the parameter of the second trajectory (6-4-5) and the parameter of the fourth trajectory (6-0-5) meet the sixth preset condition, the heart rhythm type is the ventricular tachycardia.

Optionally, a condition of determining the ventricular tachycardia herein may be the same as a condition of determining the ventricular tachycardia in step 305.1. A specific description may be obtained with reference to the foregoing description.

For example, when $(num_{123}+num_{645})<Th\_num1$, if $(num_{123}+num_{103})\geq Th\_num2$, both $sd_{123}$ and $sd_{103}$ are less than or equal to the threshold Th_sd2, and $mean\theta_{123}<mean\theta_{103}$, or if $(num_{645}+num_{605})\geq Th\_num2$, both $sd_{645}$ and $sd_{605}$ are less than or equal to the threshold Th_sd2, and $mean\theta_{645}<mean\theta_{605}$, it is the ventricular tachycardia.

In a possible implementation, the heart rhythm type is the bigeminy when a parameter of the fifth trajectory (2-4) and a parameter of the sixth trajectory (4-2) meet an eighth preset condition and a distance standard deviation parameter of the fifth trajectory (2-4) and a distance standard deviation parameter of the sixth trajectory (4-2) meet a ninth preset condition.

Optionally, that a parameter of the fifth trajectory (2-4) and a parameter of the sixth trajectory (4-2) meet an eighth preset condition includes: a minimum value of a quantity parameter of the fifth trajectory and a quantity parameter of the sixth trajectory being greater than or equal to a third quantity threshold, and an angle standard deviation parameter of the fifth trajectory and an angle standard deviation parameter of the sixth trajectory being both less than or equal to a third angle standard deviation threshold.

Optionally, that a distance standard deviation parameter of the fifth trajectory (2-4) and a distance standard deviation parameter of the sixth trajectory (4-2) meet a ninth preset condition includes: the distance standard deviation parameter of the fifth trajectory being less than or equal to a first distance standard deviation threshold, and the distance standard deviation parameter of the sixth trajectory being less than or equal to the first distance standard deviation threshold.

For example, when min $(num_{24}, num_{42})\geq$, Th_num3, $sd_{24}\leq Th\_sd3$, and $sd_{42}\leq Th\_sd3$, it is the bigeminy if $sd\_d_{24}\leq Th\_d1$, $sd\_d_{42}\leq Th\_d1$.

Figure 9:
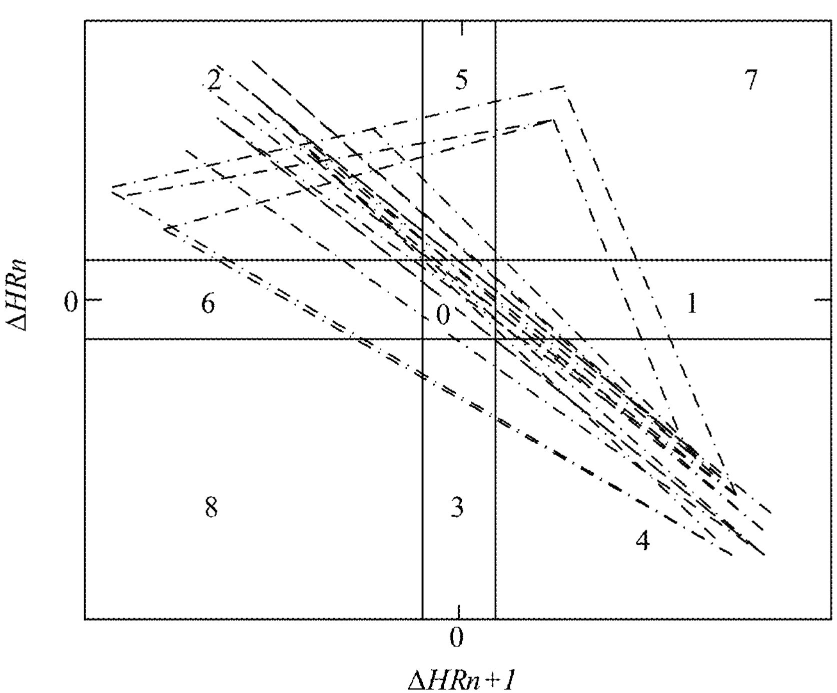
FIG. 9 is a schematic diagram of a heart rate difference trajectory of a premature beat with bigeminy according to an embodiment of this application.

FIG. 9 is a schematic diagram of a heart rate difference trajectory of a premature beat with bigeminy. As can be seen from FIG. 9, there is overlap in the bigeminy, mainly concentrated in regions '2-4' and '4-2'. The bigeminy may be recognized according to $\theta_{24}$, $\theta_{42}$, $num_{24}$, $num_{42}$, $sd_{24}$, $sd_{42}$, $sd\_d_{24}$, and $sd\_d_{42}$.

Therefore, based on the heart rhythm detection method according to this embodiment of this application, the bigeminy can be accurately recognized, and the user experience can be improved.

In a possible implementation, the heart rhythm type is the trigeminy when the parameter of the fifth trajectory (2-4) and the parameter of the sixth trajectory (4-2) meet the eighth preset condition and the distance standard deviation parameter of the fifth trajectory (2-4) and the distance standard deviation parameter of the sixth trajectory (4-2) do not meet the ninth preset condition.

Optionally, the possible implementation in which the parameter of the fifth trajectory (2-4) and the parameter of the sixth trajectory (4-2) meet the eighth preset condition may be obtained with reference to the above description when the heart rhythm type is determined as the bigeminy. Details are not described herein again.

Optionally, that the distance standard deviation parameter of the fifth trajectory (2-4) and the distance standard deviation parameter of the sixth trajectory (4-2) do not meet the ninth preset condition includes: the distance standard deviation parameter of the fifth trajectory being greater than the first distance standard deviation threshold, and the distance standard deviation parameter of the sixth trajectory being greater than the first distance standard deviation threshold.

For example, when min $(num_{24}, num_{42})\geq Th\_num3$, $sd_{24}\leq Th\_sd3$, and $sd_{42}\leq Th\_sd3$, it is the trigeminy if $sd\_d_{24}>Th\_d1$, $sd\_d_{42}>Th\_d1$.

Figure 10:
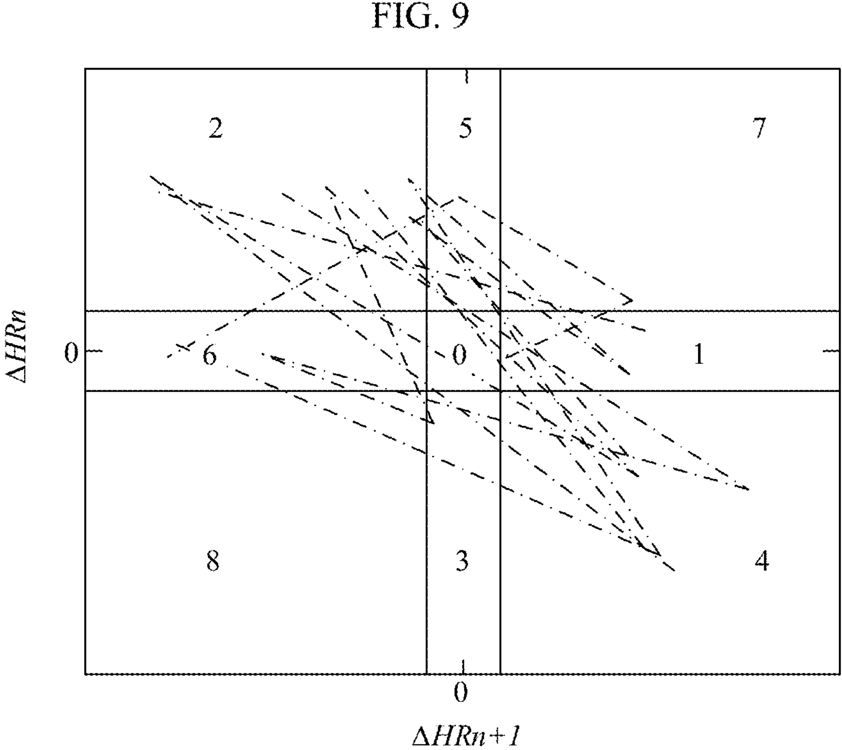
FIG. 10 is a schematic diagram of a heart rate difference trajectory of a premature beat with trigeminy according to an embodiment of this application.

FIG. 10 is a schematic diagram of a heart rate difference trajectory of a premature beat with trigeminy. As can be seen from FIG. 10, there is also overlap in the trigeminy, mainly concentrated in regions '2-4' and '4-2'. The trigeminy may be recognized according to $\theta_{24}$, $\theta_{42}$, $num_{24}$, $num_{42}$, $sd_{24}$, $sd_{42}$, d $sd\_d_{24}$, and $sd\_d_{42}$.

Therefore, based on the heart rhythm detection method according to this embodiment of this application, the trigeminy can be accurately recognized, and the user experience can be improved.

In a possible implementation, the heart rhythm type is the premature beat when the parameter of the first trajectory (1-2-3) and the parameter of the second trajectory (6-4-5) meet the second preset condition and a parameter of the seventh trajectory (1-2), a parameter of the eighth trajectory (2-3), a parameter of the ninth trajectory (6-4), and a parameter of the tenth trajectory (4-5) meet a tenth preset condition.

Optionally, that the parameter of the first trajectory (1-2-3) and the parameter of the second trajectory (6-4-5) meet the second preset condition includes: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold.

Optionally, that a parameter of the seventh trajectory (1-2), a parameter of the eighth trajectory (2-3), a parameter of the ninth trajectory (6-4), and a parameter of the tenth trajectory (4-5) meet a tenth preset condition includes: a maximum value of an angle standard deviation parameter of the seventh trajectory, an angle standard deviation parameter of the eighth trajectory, an angle standard deviation parameter of the ninth trajectory, and an angle standard deviation parameter of the tenth trajectory being less than or equal to a fourth angle standard deviation threshold.

For example, when $(num_{123}+num_{645})\geq Th\_num1$, at least one of $sd_{123}$ and $sd_{645}$ is greater than the threshold Th_sd1, and $\max(sd_{12}, sd_{23}, sd_{64}, sd_{45})\leq Th\_sd4$, it is a premature beat signal.

In a possible implementation, the heart rhythm type is the atrial fibrillation when the parameter of the first trajectory (1-2-3) and the parameter of the second trajectory (6-4-5) meet the second preset condition, the parameter of the seventh trajectory (1-2), the parameter of the eighth trajectory (2-3), the parameter of the ninth trajectory (6-4), and the parameter of the tenth trajectory (4-5) do not meet the tenth preset condition, and the first probability parameter meets an eleventh preset condition or a first quantity meets a twelfth preset condition.

Optionally, the possible implementation in which the parameter of the first trajectory (1-2-3) and the parameter of the second trajectory (6-4-5) meet the second preset condition may be obtained with reference to the above description. Details are not described herein again.

Optionally, that the parameter of the seventh trajectory (1-2), the parameter of the eighth trajectory (2-3), the parameter of the ninth trajectory (6-4), and the parameter of the tenth trajectory (4-5) do not meet the tenth preset condition includes: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold.

Optionally, that the first probability parameter meets an eleventh preset condition includes: the first probability parameter being less than a third probability threshold.

Optionally, that a first quantity meets a twelfth preset condition includes: the first quantity being greater than or equal to a fourth quantity threshold.

For example, when $(num_{123}+num_{645}) \geq Th\_num1$, at least one of $sd_{123}$ and $sd_{645}$ is greater than the threshold Th_sd1, $max(sd_{12}, sd_{23}, sd_{64}, sd_{45}) > Th\_sd4$, and $r_{zero} < Th\_r3$ or $num_{outside} \geq Th\_num4$, it is the atrial fibrillation.

In a possible implementation, the heart rhythm type is the sinus rhythm when the parameter of the first trajectory (1-2-3) and the parameter of the second trajectory (6-4-5) meet the second preset condition, the parameter of the seventh trajectory (1-2), the parameter of the eighth trajectory (2-3), the parameter of the ninth trajectory (6-4), and the parameter of the tenth trajectory (4-5) do not meet the tenth preset condition, and the first probability parameter does not meet the eleventh preset condition or the first quantity does not meet the twelfth preset condition.

Optionally, the possible implementation in which the parameter of the first trajectory (1-2-3) and the parameter of the second trajectory (6-4-5) meet the second preset condition may be obtained with reference to the above description. Details are not described herein again.

Optionally, the possible implementation in which the parameter of the seventh trajectory (1-2), the parameter of the eighth trajectory (2-3), the parameter of the ninth trajectory (6-4), and the parameter of the tenth trajectory (4-5) do not meet the tenth preset condition may be obtained with reference to the above description. Details are not described herein again.

Optionally, that the first probability parameter does not meet the eleventh preset condition includes: the first probability parameter being no less than the third probability threshold, or the first probability parameter being greater than or equal to the third probability threshold.

Optionally, that the first quantity does not meet the twelfth preset condition includes: the first quantity being less than the fourth quantity threshold.

For example, when $(num_{123}+num_{645}) \geq Th\_num1$, at least one of $sd_{123}$ and $sd_{645}$ is greater than the threshold Th_sd1, $max(sd_{12}, sd_{23}, sd_{64}, sd_{45}) > Th\_sd4$, and $r_{zero} \geq Th\_r3$ or $num_{outside} < Th\_num4$, it is the sinus rhythm.

A unified description is made herein, and the above possible implementations or examples of various preset conditions do not constitute a limitation on the embodiments of this application.

It should be understood that the division of "equal to" in each implementation is merely an exemplary description and does not constitute a limitation on the protection scope of the embodiments of this application. For example, in some cases, "equal to" and "greater than" belong to a same category, and in fact, as another implementation, "equal to" may alternatively be classified into "less than", which is not specifically limited in the embodiments of this application. For example, $(num_{123}+num_{645}) \geq Th\_num1$ above is merely a possible implementation, and as another implementation, "$(num_{123}+num_{645}) = Th\_num1$" may alternatively be classified into "$(num_{123}+num_{645}) < Th\_num1$".

In this embodiment of this application, the PPG signal with the first preset duration is acquired, according to a trajectory of changes in a heart rate difference of the PPG signal with the first preset duration, a parameter (including, but not limited to, an angle, a quantity, an angle standard deviation, and a distance standard deviation) of the trajectory is obtained, and then a heart rhythm type is determined based on the parameter of the trajectory. Compared with recognition according to each heart rate (or a cardiac waveform), according to this embodiment of this application, the recognition is based on a heart rate of a signal (that is, the PPG signal with the first preset duration), which can improve accuracy of recognition of the premature beat or atrial fibrillation, reduce a probability of recognizing the premature beat as the atrial fibrillation, and improve user experience.

For ease of understanding, the following is described with reference to interfaces in FIG. 11A, FIG. 11B, and FIG. 12.

Figure 11A:
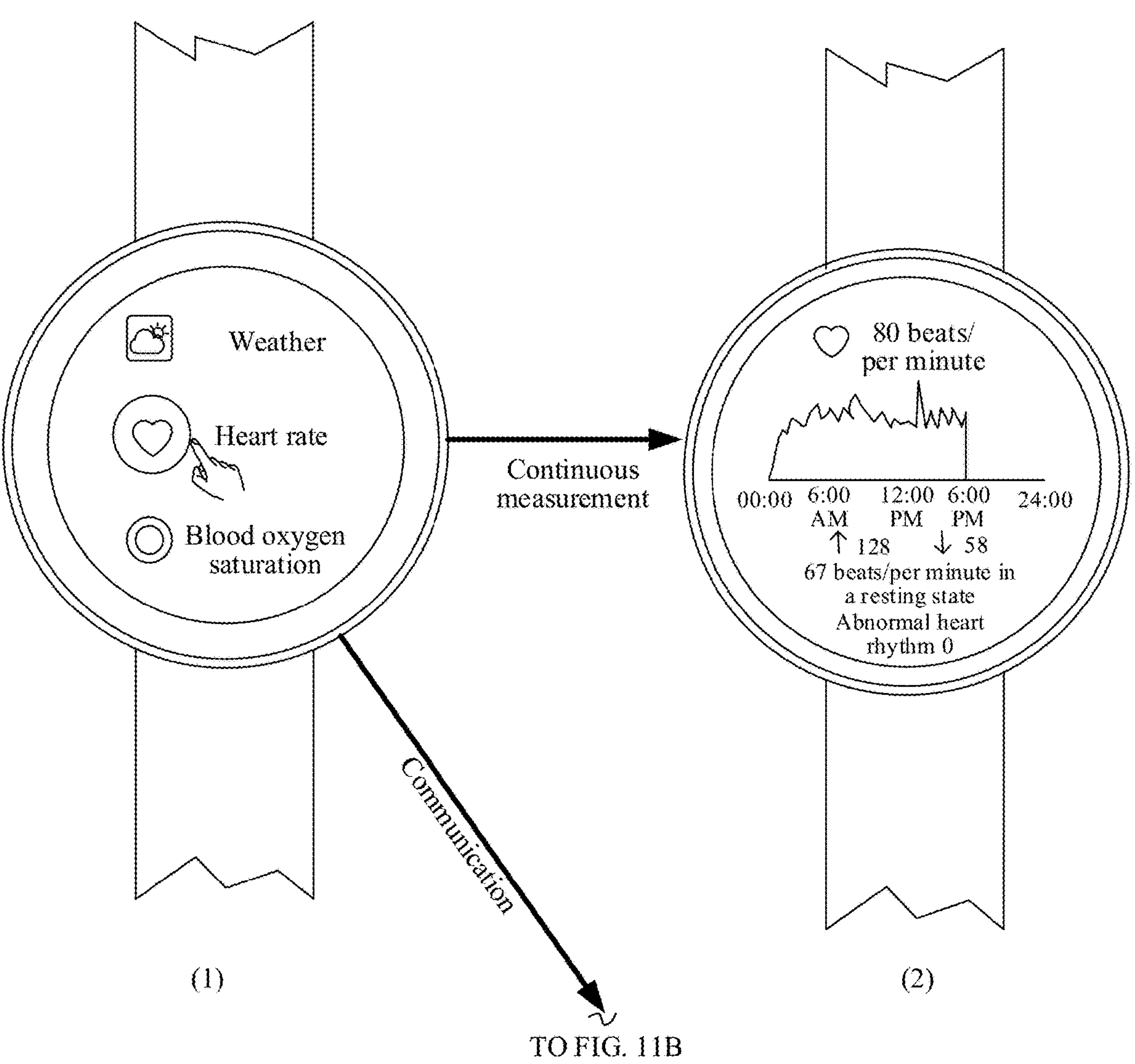
Figure 11B:
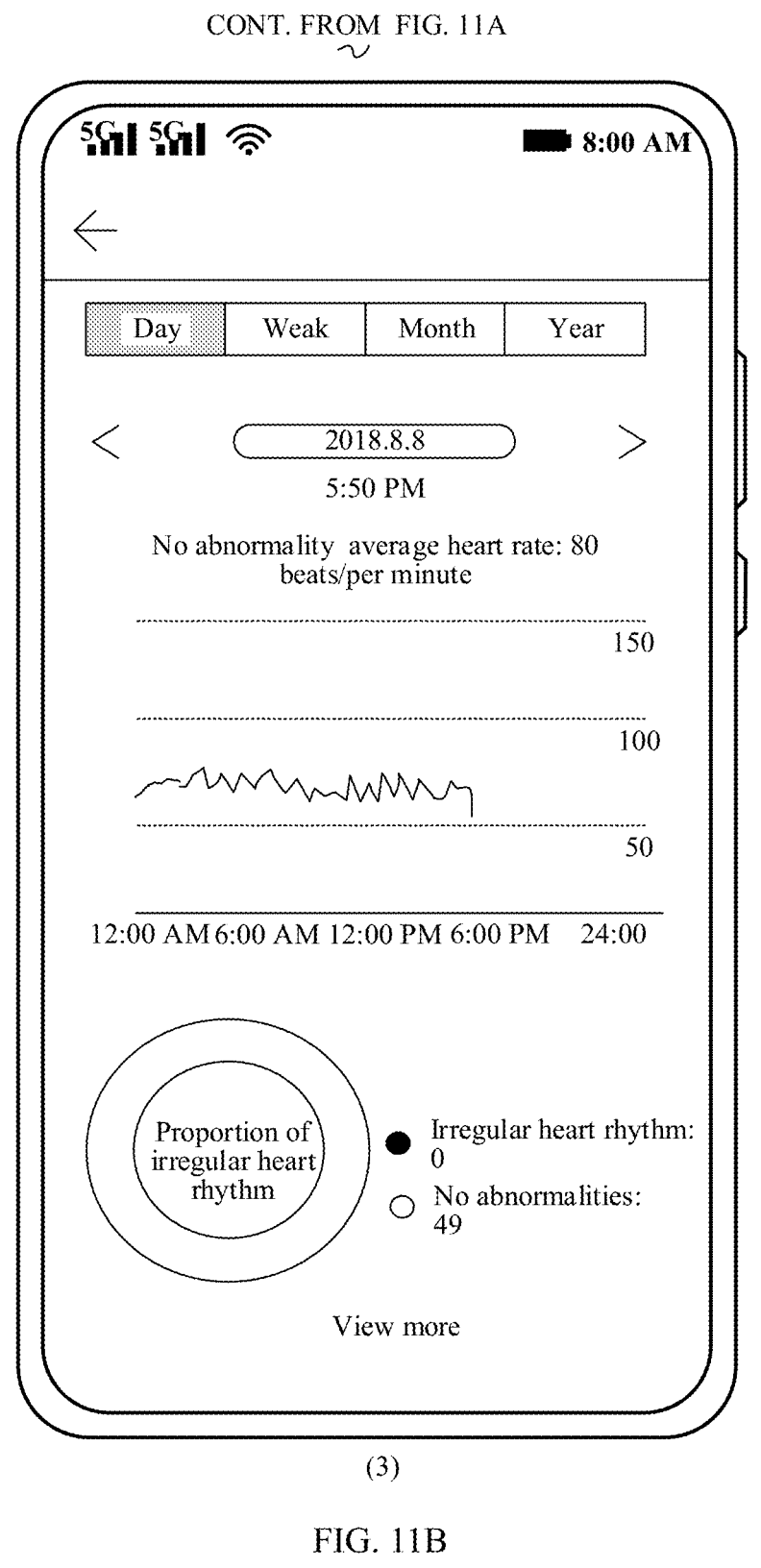

FIG. 11A and FIG. 11B are an exemplary diagram of an interface of heart rhythm detection according to an embodiment of this application.

As shown in (1) in FIG. 11A, in a state that the user wears the watch, the user can click on a heart rate application in an interface of the watch. The heart rate application may perform continuous heart rate measurement. It should be understood that the interface of (1) in FIG. 11A shows only icons of part of applications, such as weather and blood oxygen saturation, but this does not constitute a limitation on the embodiments of this application.

In a possible implementation, the user can enable an option of continuous heart rate measurement through a mobile phone in a case that the watch is connected to the mobile phone. After the option of continuous heart rate measurement is enabled, the watch may perform user heart rate monitoring for 24 hours, and can display a 24-hour heart rate curve and resting heart rate.

In a case of continuous heart rate measurement, the interface of the watch may be shown in (2) in FIG. 11A. In the interface shown in (2) in FIG. 11A, the watch may present, to the use, a heart rate curve, a resting heart rate, and a count of abnormal heart rhythms within a certain time period.

As a possible embodiment, statistical details of the heart rate may alternatively be displayed through the mobile phone. An interface of the mobile phone may be shown as (3) in FIG. 11B. In a statistical details interface, information such as a 24-hour heart rate curve, an average heart rate, a count of irregular heart rhythms, a count of no abnormalities, and a statistical graph of proportions of irregular heart rhythms may be displayed to the user.

It may be understood that each interface in FIG. 11A and FIG. 11B are merely an exemplary description, and the embodiments of this application are not limited thereto.

Figure 12:
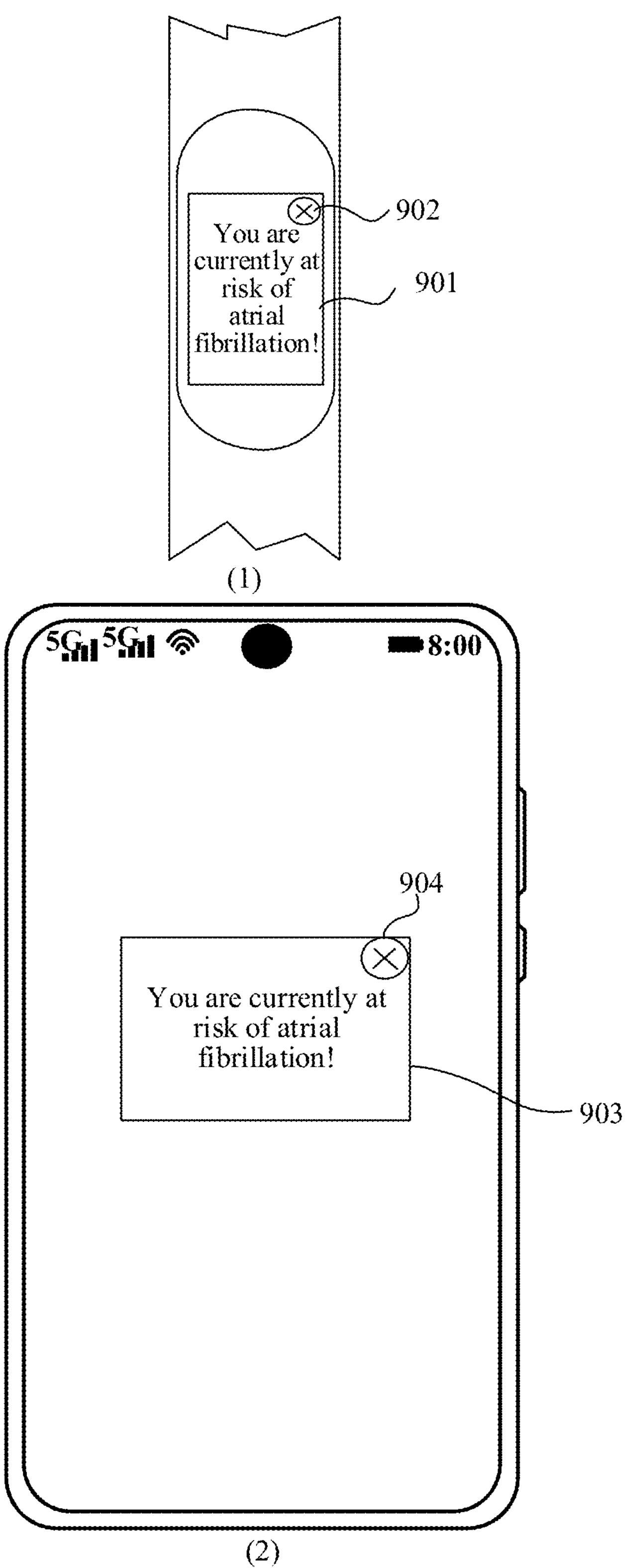
FIG. 12 is an exemplary diagram of an interface of risk warning according to an embodiment of this application.

FIG. 12 is a schematic diagram of an interface of risk warning. As a possible implementation, when an abnormal heart rhythm is detected, prompt information can be sent to the user, so that the user can know a risk of the abnormal heart rhythm in time. As shown in (1) in FIG. 12, a prompt box 901 (or a prompt window) may be sent to the user in an interface of a bracelet, and the prompt box 901 displays "You are currently at risk of atrial fibrillation!" The user, after seeing the prompt box 901, may click on 902 to close the prompt box 901.

As a possible implementation, when the mobile phone is connected to the watch or bracelet, the mobile phone can also send prompt information to the user. Similarly, as shown in (2) in FIG. 12, a prompt box 903 may also be sent to the user in the interface of the mobile phone, and the prompt box 903 displays "You are currently at risk of atrial fibrillation!" The user, after seeing the prompt box 903, may click on 904 to close the prompt box 903.

It may be understood that the interface in FIG. 12 is merely an exemplary description, and the embodiments of this application are not limited thereto.

A software system and hardware architecture to which the embodiments of this application are applied are respectively described below with reference to FIG. 13 and FIG. 14.

Figure 13:
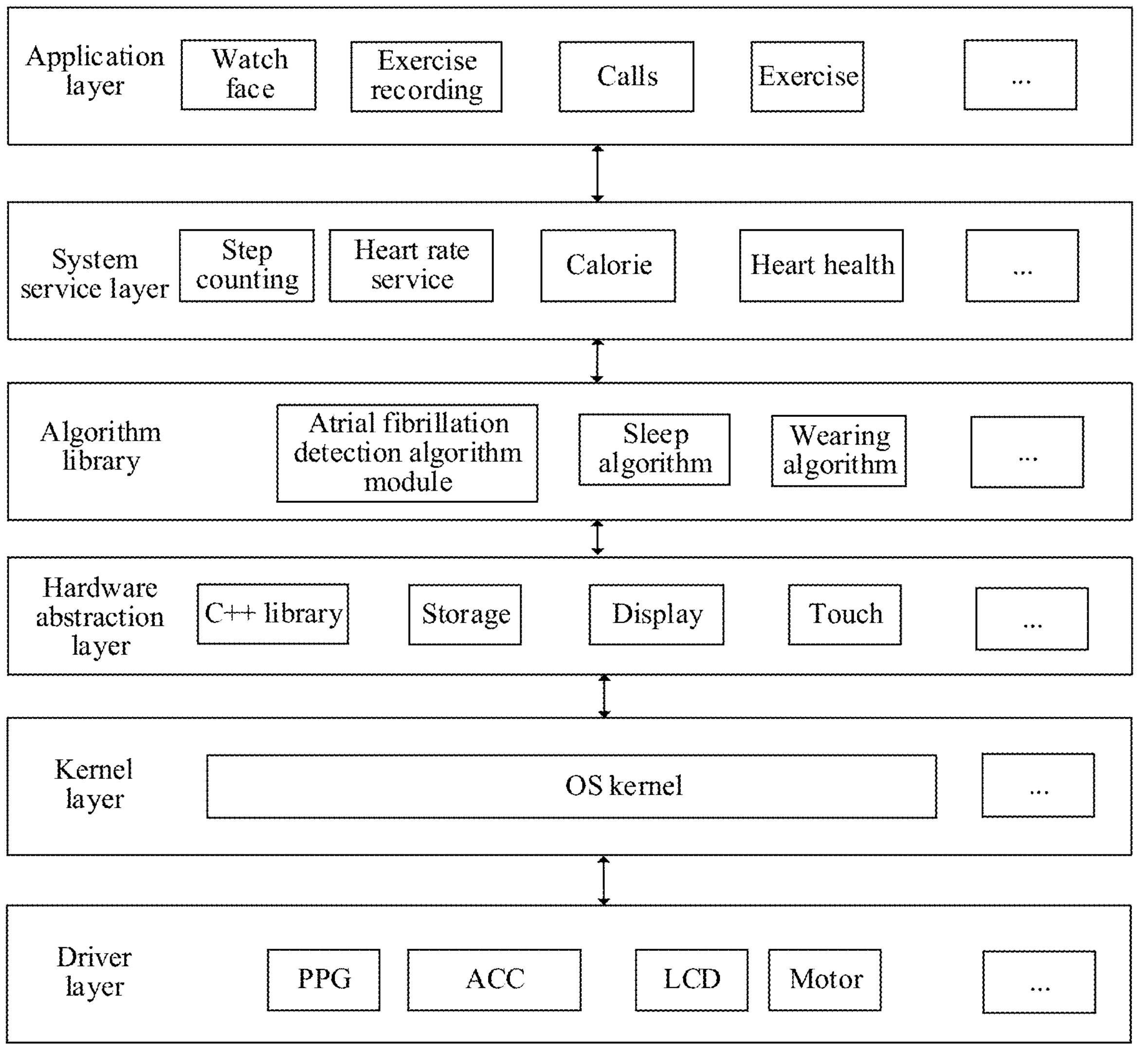
FIG. 13 is a schematic diagram of a software system to which an embodiment of this application is applied.

FIG. 13 is a schematic diagram of a software system to which an embodiment of this application is applied. As shown in FIG. 13, the software system using a layered architecture is divided into several layers, and each layer has a clear role and task. The layers communicate with each other through a software interface. In some embodiments, the software system may be divided into six layers, namely an application layer, a system service layer, an algorithm library (library), a hardware abstraction layer HAL, a kernel layer (kernel), and a driver layer (driver).

As shown in FIG. 13, the application layer includes a watch face, exercise recording, calls, and exercise.

It may be understood that, partial applications are shown in FIG. 13, and in fact the application layer may further include other applications, which is not limited in this application. For example, the application layer further includes applications such as message, alarm clock, weather, stopwatch, compass, timer, flashlight, calendar, and Alipay.

As shown in FIG. 13, the system service layer includes step counting, heart rate service, calorie, heart health, and the like.

The algorithm library may include a plurality of algorithmic modules. For example, as shown in FIG. 13, the algorithm library includes an atrial fibrillation detection algorithm module, a sleep algorithm, a wearing algorithm, and the like.

The atrial fibrillation detection algorithm module is configured to determine a heart rhythm type, so as to accurately recognize atrial fibrillation or a premature beat. As a possible implementation, the atrial fibrillation detection algorithm module is configured to perform the foregoing method shown in FIG. 3.

The wearing algorithm is used for detecting a wearing state of the watch.

As shown in FIG. 13, the hardware abstraction layer includes a C++ library, storage, display, touch, and the like. The C++ library is used for providing system resources for the algorithm library.

It may be understood that the hardware abstraction layer shown in FIG. 13 is partial content, and in fact the hardware abstraction layer HAL may further include other content, such as a Bluetooth module, a GPS module, and the like.

As shown in FIG. 13, the kernel layer includes an OS kernel. The OS kernel is used for performing management and scheduling.

The driver layer is used for driving hardware resources. The driver layer may include a plurality of driver modules. As shown in FIG. 13, the driver layer includes a PPG driver, an LCD driver, a motor, and the like.

For example, a user can click on an exercise application. As the user is exercising, the exercise application can display the heart rate to the user in real time through an interface. A process of heart rhythm monitoring according to an embodiment of this application is described below with reference to FIG. 13. When the user clicks on the heart rate application, the application layer invokes the heart rate service in the system service layer after receiving an operation of the user. The OS kernel schedules an ACC driver so that an ACC sensor acquires an ACC signal to determine whether to enter an atrial fibrillation detection procedure. The OS kernel schedules the PPG driver, so that the PPG sensor lights up to acquire data (or a PPG signal). The PPG driver can return the acquired data to the OS kernel. The OS kernel sends the acquired data to the algorithm library to perform a relevant calculation. The wearing algorithm module in the algorithm library detects whether the watch is worn based on the PPG signal and reports a wearing result to the OS kernel. If it is detected that the user wears the watch, the OS kernel triggers the execution of a heart rate monitoring service. The OS kernel sends the PPG signal acquired by the PPG sensor to the atrial fibrillation detection algorithm module. The atrial fibrillation detection algorithm module calculates the heart rate and confidence of the heart rate based on the PPG signal. The atrial fibrillation detection algorithm module returns the heart rhythm type to the OS kernel. The OS kernel reports the heart rhythm type to the application layer. The application layer displays the heart rhythm type reported by the OS kernel on the UI interface.

Figure 14:
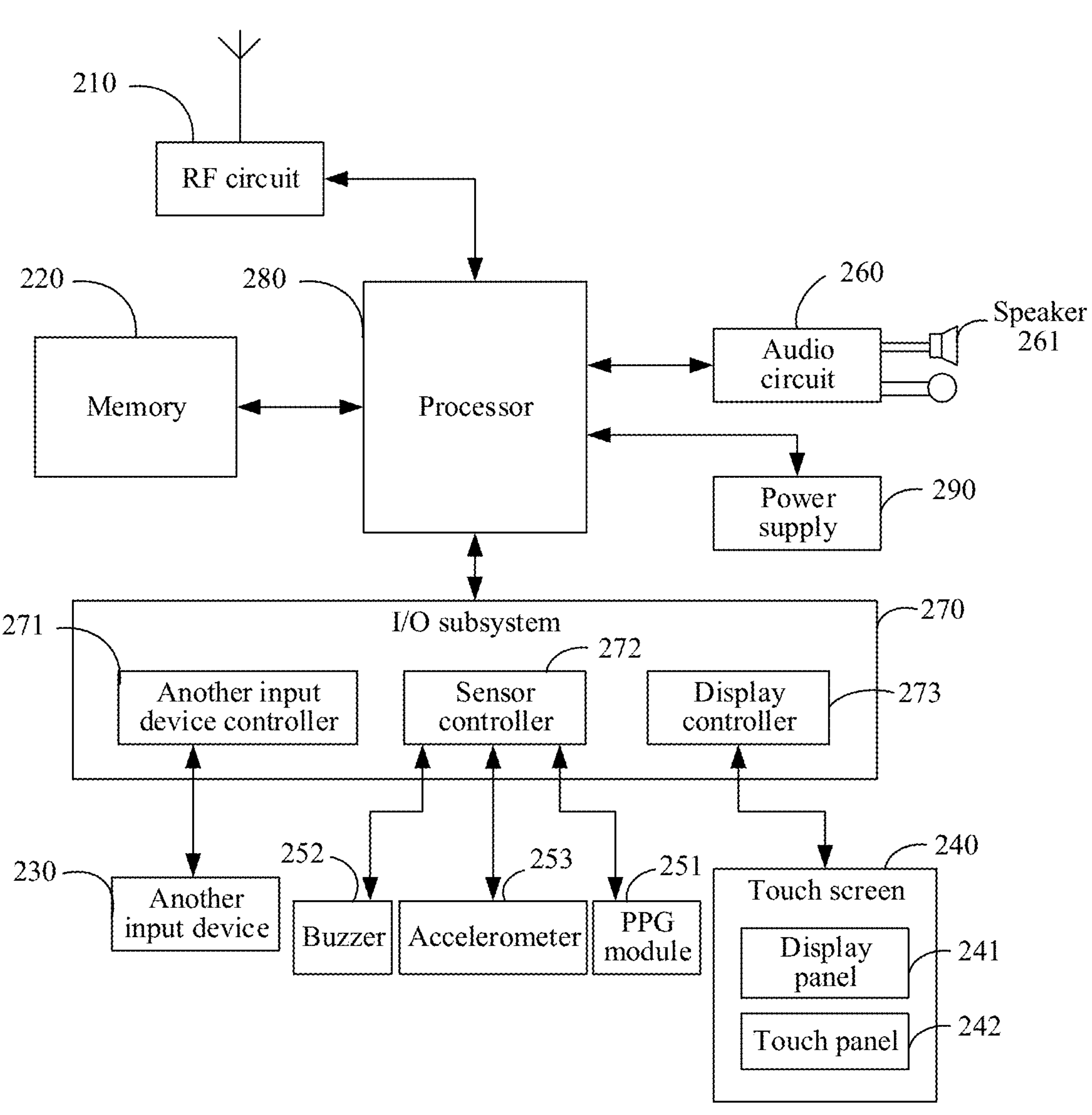
FIG. 14 is a schematic structural diagram of an apparatus applied to an embodiment of this application.

FIG. 14 is a schematic structural diagram of an apparatus 500 applied to an embodiment of this application. The apparatus 500 may be a watch, a wristband, a wearable electronic device, another wearable device for measuring a heart rate, or the like. The specific type of the apparatus 500 is not limited in this embodiment of this application.

As shown in FIG. 14, the apparatus 500 may include components such as a radio frequency (radio frequency, RF) circuit 210, a memory 220, another input device 230, a touch screen 240, a PPG module 251, a buzzer 252, an accelerometer 253, an audio circuit 260, an I/O subsystem 270, a processor 280, and a power supply 290.

It should be noted that the structure shown in FIG. 14 does not constitute a specific limitation on the apparatus 500. In some other embodiments of this application, the apparatus 500 may include more or fewer components than the components shown in FIG. 14, or the apparatus 500 may include a combination of some components in the components shown in FIG. 14, or the apparatus 500 may include sub-components of some components in the components shown in FIG. 14. The components shown in FIG. 14 may be implemented by hardware, software, or a combination of software and hardware.

The RF circuit 210 may be configured to send and receive signals during an information receiving and sending process or a call process. For example, after downlink information of a base station is received, the downlink information is sent to the processor 280 for processing. In addition, uplink data is sent to the base station. Generally, the RF circuit includes, but is not limited to, an antenna, at least one amplifier, a transceiver, a coupler, a low noise amplifier (low noise amplifier, LNA), a duplexer, and the like. In addition, the RF circuit 210 may also communicate with a network and another device through wireless communication. The wireless communication may use any communication standard or protocol, which includes, but is not limited to, Global System for Mobile Communications (global system of mobile communication, GSM), General Packet Radio Service (general packet radio service, GPRS), Code Division Multiple Access (code division multiple access, CDMA), Wideband Code Division Multiple Access (wideband code division multiple access, WCDMA), Long Term Evolution (long term evolution, LTE), e-mail, a short messaging service (short messaging service, SMS), and the like.

The memory 220 may be configured to store a software program. By running the software program stored in the memory 220, the processor 280 performs various functions of the apparatus 500. The memory 220 may mainly include a program storage region and a data storage region. The program storage region may store an operating system, an application required by at least one function (for example, a sound playback function and an image display function), and the like. The data storage region may store data (for example, audio data and an address book) maintained according to the use of the apparatus 500, and the like. In addition, the memory 220 may include a high-speed random access memory, and may further include a non-volatile memory, such as at least one magnetic disk storage device, a flash storage device, or another volatile solid-state storage device.

The another input device 230 may be configured to receive input digit or character information, and generate a keyboard signal input related to user setting and function control of the apparatus 500. Specifically, the another input device 230 may include, but is not limited to, one or more of a physical keyboard, a function key (such as a volume control key or a power on/off key), a trackball, a mouse, a joystick, an optical mouse (the optical mouse is a touch-sensitive surface that does not display a visible output, or an extension of a touch-sensitive surface formed by a touch screen), and the like. The another input device 230 is connected to another input device controller 271 of the I/O subsystem 270, and exchanges a signal with the processor 280 under control of the another device input controller 271.

The touch screen 240 may be configured to display information entered by a user or information provided to the user, and various menus of the apparatus 500, and may further receive a user input. Specifically, the touch screen 240 may include a display panel 241 and a touch panel 242. The display panel 241 may be a liquid crystal display (liquid crystal display, LCD), an organic light-emitting diode (organic light-emitting diode, OLED), an active-matrix organic light-emitting diode (active-matrix organic light-emitting diode, AMOLED), a flex light-emitting diode (flex light-emitting diode, FLED), a mini light-emitting diode (mini light-emitting diode, Mini LED), a micro light-emitting diode (micro light-emitting diode, Micro LED), a micro OLED (Micro OLED), or a quantum dot light emitting diode (quantum dot light emitting diodes, QLED).

The touch panel 242, also referred to as a display screen, a touch-sensitive screen, or the like, may collect a touch or non-touch operation (such as an operation performed by the user on the touch panel 242 or near the touch panel 242 by using any proper object or accessory such as a finger or a stylus, or a somatosensory operation, where the operation includes an operation type such as a single-point control operation or a multipoint control operation) of the user on or near the touch panel, and drive a corresponding connection apparatus based on a preset program. Optionally, the touch panel 242 may include two parts: a touch detection apparatus and a touch controller. The touch detection apparatus detects a gesture of the user, that is, a touch position and posture, detects a signal generated by the touch operation, and transmits the signal to the touch controller. The touch controller receives touch information from the touch detection apparatus, converts the touch information into information that can be processed by the processor, and then transmits the information to the processor 280, and can receive and execute a command transmitted by the processor 280. In addition, the touch panel 242 may be implemented in various types, such as a resistive type, a capacitive type, an infrared type, or a surface sound wave type, or the touch panel 242 may be implemented by using any technology developed in the future. Further, the touch panel 242 may cover the display panel 241. The user may perform, according to content displayed on the display panel 241 (the displayed content includes, but is not limited to, a soft keyboard, a virtual mouse, a virtual key, an icon, and the like), an operation on or near the touch panel 242 covering the display panel 241. After detecting the operation on or near the touch panel 242, the touch panel 242 transmits the operation to the processor 280 through the I/O subsystem 270, to determine the user input. Subsequently, the processor 280 provides a corresponding visual output on the display panel 241 through the I/O subsystem 270 according to the user input. Although, in FIG. 14, the touch panel 242 and the display panel 241 are used as two separate components to implement input and output functions of the apparatus 500, in some embodiments, the touch panel 242 and the display panel 241 may be integrated to implement the input and output functions of the apparatus 500.

Prompt information such as a wearing manner and wearing state, and historical information of a visual form (number, table, and graphic) or an audible form (synthetic speech or tune) of detected heart rate may be provided on the display panel 241 under control of a program of the processor 280. As a non-limiting example, a visual graph may be displayed. The visual graph shows the heart rate calculated every 5 minutes at a previous fixed time interval (for example, 1 hour) or after an exercise period has ended (for example, determined by an instruction from the user). Average heart rate information or heart rate statistical information during a previous time period or a plurality of time periods may further be provided on the display panel 241 under control of the processor 280. As another example, a current heart rate value may be provided on the display panel 241 as a "real-time" heart rate value that is periodically (for example, per second) displayed to the user during an ongoing exercise plan.

The PPG module 251 includes a light emitter and a light sensor. The measurement of heart rate by the PPG module is based on the principle of light absorption by substances. The light emitter in the PPG module of the electronic device irradiates blood vessels of skin, and the light sensor receives light transmitted from the skin. Since different volumes of blood in the blood vessels absorb green light differently, at the time of heart beating, the blood flow increases, and the amount of absorbed green light increases accordingly; and at the time of interval between two heart beats, the blood flow decreases, and the amount of absorbed green light decreases accordingly. Therefore, the heart rate can be measured according to light absorbance of the blood. In operation, the light emitter may transmit a light beam to the skin of the user, and the light beam may be reflected by the skin of the user and received by the light sensor. The light sensor may convert the light into an electrical signal that indicates intensity of the light. The electrical signal may be in an analog form and may be converted to a digital form by an analog-to-digital converter. A digital signal from the analog-to-digital converter may be a time-domain PPG signal fed to the processor 280. An output of an accelerometer may further be converted to a digital form by the analog-to-digital converter. The processor 280 may receive a digital signal from the light sensor, and digitize an accelerometer output signal of the accelerometer, and may process the signals to provide a heart rate or wearing state output signal to a storage device, a visual display, an audible annunciator, the touch screen, or another output indicator.

The apparatus 500 may further include at least one sensor such as the light sensor, a motion sensor, and other sensors. Specifically, the light sensor may include an ambient light sensor and a proximity sensor, where the ambient light sensor may adjust luminance of the display panel 241 according to brightness of ambient light. The proximity sensor may switch off backlight of the display panel 241 and/or the touch panel 242 when the apparatus 500 is moved to an ear. As a type of motion sensor, an accelerometer sensor may detect a magnitude of acceleration in various directions (generally three axes), and may detect a magnitude and a direction of gravity when static, which may be used for a function related to vibration identification (such as a pedometer and a knock), and the like. For other sensors such as a gyroscope, a barometer, a hygrometer, a thermometer, an infrared sensor, and the like that may further be configured on the apparatus 500, details are not described herein again.

The apparatus 500 may further include the buzzer 252, which may generate vibrations according to an instruction of the processor 280.

The audio circuit 260 may provide an audio interface between the user and the apparatus 500. The audio circuit 260 may transmit the received converted audio data into a speaker 261. The speaker 261 converts the signal into a sound signal and output the sound signal. On the other hand, a microphone converts the collected sound signal into a signal. The audio circuit 260 receives the signal, converts the signal into the audio data, and then outputs the audio data to the RF circuit 210 to send the audio data to, for example, a mobile phone, or outputs the audio data to the memory 220 for further processing.

The I/O subsystem 270 is configured to control external input and output devices, and may include the another device input controller 271, a sensor controller 272, and a display controller 273. Optionally, one or more another input control device controllers 271 receive a signal from the another input device 230 and/or send a signal to the another input device 230. The another input device 230 may include a physical button (a pressing button, a rocker button, or the like), a dial pad, a slider switch, a joystick, a click scroll wheel, or an optical mouse (the optical mouse may be a touch-sensitive surface that does not display a visible output, or an extension of a touch-sensitive surface formed by a touch screen). It should be noted that the another input control device controller 271 may be connected to any one or more of the foregoing devices. The display controller 273 in the I/O subsystem 270 receives a signal from the touch screen 240 or sends a signal to the touch screen 240. After the touch screen 240 detects the user input, the display controller 273 converts the detected user input into interaction with an object displayed on a user interface of the touch screen 240. That is, man-machine interaction is implemented. The sensor controller 272 may receive a signal from one or more sensors 251 and/or may send a signal to the one or more sensors 251.

The processor 280 is a control center of the apparatus 500, and is connected to various parts of the mobile phone by using various interfaces and lines. By running or executing the software program and/or modules stored in the memory 220, and invoking data stored in the memory 220, the processor 280 performs various functions and data processing of the apparatus 500. Optionally, the processor 280 may include one or more processing units. For example, the processor 110 may include at least one of the following processing units: an application processor (application processor, AP), a modem processor, a graphics processing unit (graphics processing unit, GPU), an image signal processor (image signal processor, ISP), a controller, a video codec, a digital signal processor (digital signal processor, DSP), a baseband processor, and a neural-network processing unit (neural-network processing unit, NPU). Different processing units may be separate devices, or may be an integrated device.

Optionally, the processor 280 may integrate the application processor and the modem processor. The application processor mainly processes an operating system, a user interface, an application, and the like. The modem processor mainly processes wireless communication. It may be understood that the modem processor may alternatively not be integrated into the processor 280.

The apparatus 500 further includes the power supply 290 (such as a battery) for supplying power to the components. Optionally, the power supply may be logically connected to the processor 280 through a power management system, thereby implementing functions such as charging, discharging, and power consumption management through the power management system. It should be understood that, although not shown in the figure, the apparatus 500 may further include a camera, a Bluetooth module, and the like, and details are not described herein.

The modules stored in the memory 220 may include: an operating system, a contact/motion module, a graphic module, applications, and the like.

The contact/motion module is configured to detect contact of an object or a finger with the touch screen 240 or a click-type touch wheel, capture a speed (direction and magnitude) and an acceleration (a change in magnitude or direction) of the contact, and determine the type of a contact event. For example, there are a plurality of contact event detection modules, and sometimes a gesture is combined with an element in the user interface to implement some operations: finger pinching/depinching (pinching/depinching), and the like.

The graphic module is configured to render and display a graphic on the touch screen or another display, where the graphic includes a web page, an icon, a digital image, a video, and an animation.

The applications may include contacts, phone, video conference, email client, instant messaging, personal motion, camera, image management, video player, music player, calendar, plug-ins (for example, weather, stocks, calculator, clock, and dictionary), custom plug-ins, search, note, map, online video, and the like.

It may be understood that, a connection relationship between the modules shown in FIG. 14 is merely an exemplary description, and does not constitute a limitation on the connection relationship between the modules of the apparatus 500. Optionally, the modules of the apparatus 500 may alternatively be a combination of the plurality of connection manners in the foregoing embodiments.

As can be seen from the above, in this embodiment of this application, the first PPG signal with the first preset duration is acquired, heart rate values are then determined based on the first PPG signal, a scatter plot is generated by using the heart rate differences, to obtain a trajectory of changes in the heart rate differences, and the heart rhythm type is determined based on parameters derived from the trajectory of changes in the heart rate differences (including, but not limited to, an angle, a quantity, an angle standard deviation, and a distance standard deviation), which can accurately recognize the heart rhythm type, improve accuracy of recognition of a premature beat or atrial fibrillation, prevent recognition of a premature beat signal as an atrial fibrillation signal, and improve user experience.

This application further provides a computer program product, where the computer program product, when executed by a processor, implements the method according to any method embodiment of this application.

The computer program product may be stored in a memory, and subjected to processing procedures such as preprocessing, compiling, assembling, and linking, to be eventually converted into an executable target file that can be executed by the processor.

This application further provides a computer-readable storage medium, storing a computer program, where the computer program, when executed by a computer, implements the method according to any method embodiment of this application. The computer program may be a high-level language program or an executable target program.

The computer-readable storage medium may be a volatile memory or non-volatile memory, or may include both a volatile memory and a non-volatile memory. The non-volatile memory may be a read-only memory (read-only memory, ROM), a programmable ROM (programmable ROM, PROM), an erasable PROM (erasable PROM, EPROM), an electrically EPROM (electrically EPROM, EEPROM), or a flash memory. The volatile memory may be a random access memory (random access memory, RAM), and is used as an external cache. Through examples but not limitative descriptions, many forms of RAMs may be used, for example, a static RAM (static RAM, SRAM), a dynamic RAM (dynamic RAM, DRAM), a synchronous DRAM (synchronous DRAM, SDRAM), a double data rate SDRAM (double data rate SDRAM, DDR SDRAM), an enhanced SDRAM (enhanced SDRAM, ESDRAM), a synchlink DRAM (synchlink DRAM, SLDRAM), and a direct rambus RAM (direct rambus RAM, DR RAM).

It may be clearly understood by a person skilled in the art that, for ease and brief description, for a detailed working process and a generated technical effect of the foregoing apparatus and device, reference may be made to a corresponding process and technical effect in the foregoing method embodiment, and details are not described herein again.

In the several embodiments provided in this application, the disclosed system, apparatus, and method may be implemented in other manners. For example, some features of the method embodiment described above may be ignored or not be performed. The described apparatus embodiment is merely exemplary. The unit division is merely logical function division and may be other division during actual implementation, and a plurality of units or components may be combined or integrated into another system. In addition, the coupling between the units or the coupling between the components may be direct coupling or indirect coupling, and the coupling includes an electrical connection, a mechanical connection, or another form of connection.

It should be understood that sequence numbers of the processes do not mean execution sequences in various embodiments of this application. The execution sequences of the processes should be determined according to functions and internal logic of the processes, and should not constitute any limitation on the implementation processes of the embodiments of this application.

In addition, the terms "system" and "network" may be used interchangeably in this specification. The term "and/or" used in this specification describes only an association relationship for describing associated objects and represents that three relationships may exist. For example, A and/or B may represent the following three cases: the following three cases: Only A exists, both A and B exist, and only B exists. In addition, the character "/" in this specification generally indicates an "or" relationship between the associated objects.

In summary, the foregoing descriptions are merely preferred embodiments of the technical solutions of this application, but are not intended to limit the protection scope of this application. Any modification, equivalent replacement, improvement, or the like made within the spirit and principle of this application shall fall within the protection scope of this application.

What is claimed is:

1. A heart rhythm detection method, applied to an electronic device, and comprising:

acquiring a first photoplethysmograph (PPG) signal with a first preset duration of time, wherein the acquiring a first PPG signal with the first preset duration of time comprises:

acquiring a PPG signal and an accelerometer (ACC) signal with a fourth preset duration of time, the PPG signal with the first preset duration of time including a plurality of PPG signals with the fourth preset duration of time, the fourth preset duration of time being less than the first preset duration of time, determining whether the electronic device has been in a motion state within a fifth preset duration of time, the fifth preset duration of time being greater than the first preset duration of time, and continuously acquiring the PPG signal and the ACC signal with the fourth preset duration of time until an acquisition duration meets the first preset duration of time if the electronic device has not been in the motion state within the fifth preset duration of time;

determining a plurality of heart rate values based on the first PPG signal;

determining a difference of every two adjacent heart rates based on the plurality of heart rate values, the difference of every two adjacent heart rates being used for generating a heart rate difference trajectory graph;

acquiring a parameter of a heart rate difference trajectory based on the heart rate difference trajectory graph and the parameter of the heart rate difference trajectory comprising at least one of an angle, a quantity, an angle standard deviation, or a distance standard deviation;

determining a heart rhythm type of the first PPG signal according to the parameter of the heart rate difference trajectory, the heart rhythm type comprising at least one of a premature beat, atrial fibrillation, a sinus rhythm, ventricular tachycardia, bigeminy, or trigeminy; and displaying the heart rhythm type of the first PPG signal.

2. The method according to claim 1, further comprising: determining a first parameter according to the first PPG signal with the first preset duration of time, and determining whether the first parameter is greater than or equal to a first threshold;

wherein the determining a heart rhythm type of the first PPG signal according to the parameter of the heart rate difference trajectory comprises:

determining the heart rhythm type of the first PPG signal according to the first parameter and the parameter of the heart rate difference trajectory.

3. The method according to claim 2, wherein the determining the heart rhythm type of the first PPG signal according to the first parameter and the parameter of the heart rate difference trajectory comprises:

performing, when the first parameter is greater than or equal to the first threshold, first recognition based on the parameter of the heart rate difference trajectory to determine the heart rhythm type of the first PPG signal, the heart rhythm type comprising at least one of the premature beat, the atrial fibrillation, the sinus rhythm, or the ventricular tachycardia; and performing, when the first parameter is less than the first threshold, second recognition based on the parameter of the heart rate difference trajectory to determine the heart rhythm type of the first PPG signal, the heart rhythm type comprising at least one of the premature beat, the atrial fibrillation, the sinus rhythm, the ventricular tachycardia, the bigeminy, or the trigeminy.

4. The method according to claim 3, wherein in the first recognition or the second recognition, the heart rate difference trajectory comprises: a first trajectory and a second trajectory; and the heart rhythm type is the premature beat when a parameter of the first trajectory and a parameter of the second trajectory meet a first preset condition;

wherein that a parameter of the first trajectory and a parameter of the second trajectory meet a first preset condition comprises: a sum of a quantity parameter of the first trajectory and a quantity parameter of the second trajectory being greater than or equal to a first quantity threshold, and an angle standard deviation parameter of the first trajectory and an angle standard deviation parameter of the second trajectory being both less than or equal to a first angle standard deviation threshold.

5. The method according to claim 4, wherein in the first recognition, the heart rate difference trajectory comprises: the first trajectory and the second trajectory; and the heart rhythm type is the atrial fibrillation when the parameter of the first trajectory and the parameter of the second trajectory meet a second preset condition and a first probability parameter meets a third preset condition;

wherein that a parameter of the first trajectory and a parameter of the second trajectory meet a first preset condition comprises: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold;

wherein that a first probability parameter meets a third preset condition comprises: the first probability parameter being less than a first probability threshold.

6. The method according to claim 5, wherein the heart rate difference trajectory comprises: the first trajectory and the second trajectory; and the heart rhythm type is the sinus rhythm when the parameter of the first trajectory and the parameter of the second trajectory meet the second preset condition and the first probability parameter does not meet the third preset condition;

wherein that the parameter of the first trajectory and the parameter of the second trajectory meet the second preset condition comprises: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold;

wherein that the first probability parameter does not meet the third preset condition comprises: the first probability parameter being no less than the first probability threshold.

7. The method according to claim 5, wherein in the first recognition or the second recognition, the heart rate difference trajectory comprises: the first trajectory, the second trajectory, a third trajectory, and a fourth trajectory; and when the parameter of the first trajectory and the parameter of the second trajectory meet a fourth preset condition and the parameter of the first trajectory and a parameter of the third trajectory meet a fifth preset condition; or when the parameter of the first trajectory and the parameter of the second trajectory meet a fourth preset condition and the parameter of the second trajectory and a parameter of the fourth trajectory meet a sixth preset condition, the heart rhythm type is the ventricular tachycardia;

wherein that the parameter of the first trajectory and the parameter of the second trajectory meet a fourth preset condition comprises: the sum of the quantity parameter of the first trajectory and the quantity parameter of the second trajectory being less than the first quantity threshold;

wherein that the parameter of the first trajectory and a parameter of the third trajectory meet a fifth preset condition comprises: a sum of the quantity parameter of the first trajectory and a quantity parameter of the third trajectory being greater than or equal to a second quantity threshold, the angle standard deviation parameter of the first trajectory and an angle standard deviation parameter of the third trajectory being both less than or equal to a second angle standard deviation threshold, and an angle mean parameter of the first trajectory being less than that of the third trajectory;

wherein that the parameter of the second trajectory and a parameter of the fourth trajectory meet a sixth preset condition comprises: a sum of the quantity parameter of the second trajectory and the quantity parameter of the third trajectory being greater than or equal to the second quantity threshold, the angle standard deviation parameter of the second trajectory and the angle standard deviation parameter of the third trajectory being both less than or equal to the second angle standard deviation threshold, and an angle mean parameter of the second trajectory being less than that of the fourth trajectory.

8. The method according to claim 7, wherein in the first recognition, the heart rate difference trajectory comprises: the first trajectory and the second trajectory; and the heart rhythm type is the atrial fibrillation when the parameter of the first trajectory and the parameter of the second trajectory meet the fourth preset condition and the first probability parameter meets a seventh preset condition;

wherein that the parameter of the first trajectory and the parameter of the second trajectory meet the fourth preset condition comprises: the sum of the quantity parameter of the first trajectory and the quantity parameter of the second trajectory being less than the first quantity threshold;

wherein that the first probability parameter meets a seventh preset condition comprises:

the first probability parameter being less than a second probability threshold.

9. The method according to claim 8, wherein in the first recognition, the heart rate difference trajectory comprises: the first trajectory and the second trajectory; and the heart rhythm type is the sinus rhythm when the parameter of the first trajectory and the parameter of the second trajectory meet the fourth preset condition and the first probability parameter does not meet the seventh preset condition;

wherein that the parameter of the first trajectory and the parameter of the second trajectory meet the fourth preset condition comprises: the sum of the quantity parameter of the first trajectory and the quantity parameter of the second trajectory being less than the first quantity threshold;

wherein that the first probability parameter does not meet the seventh preset condition comprises: the first probability parameter being no less than the second probability threshold.

10. The method according to claim 5, wherein in the second recognition, the heart rate difference trajectory comprises: the first trajectory and the second trajectory; and the heart rhythm type is the atrial fibrillation when the parameter of the first trajectory and the parameter of the second trajectory meet the second preset condition;

wherein that the parameter of the first trajectory and the parameter of the second trajectory meet the second preset condition comprises: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first angle standard deviation threshold.

11. The method according to claim 3, wherein in the second recognition, the heart rate difference trajectory comprises: a fifth trajectory and a sixth trajectory; and the heart rhythm type is the bigeminy when a parameter of the fifth trajectory and a parameter of the sixth trajectory meet an eighth preset condition and a distance standard deviation parameter of the fifth trajectory and a distance standard deviation parameter of the sixth trajectory meet a ninth preset condition;

wherein that a parameter of the fifth trajectory and a parameter of the sixth trajectory meet an eighth preset condition comprises: a minimum value of a quantity parameter of the fifth trajectory and a quantity parameter of the sixth trajectory being greater than or equal to a third quantity threshold, and an angle standard deviation parameter of the fifth trajectory and an angle standard deviation parameter of the sixth trajectory being both less than or equal to a third angle standard deviation threshold;

wherein that a distance standard deviation parameter of the fifth trajectory and a distance standard deviation parameter of the sixth trajectory meet a ninth preset condition comprises: the distance standard deviation parameter of the fifth trajectory being less than or equal to a first distance standard deviation threshold, and the distance standard deviation parameter of the sixth trajectory being less than or equal to the first distance standard deviation threshold.

12. The method according to claim 11, wherein in the second recognition, the heart rate difference trajectory comprises: the fifth trajectory and the sixth trajectory; and the heart rhythm type is the trigeminy when the parameter of the fifth trajectory and the parameter of the sixth trajectory meet the eighth preset condition and the distance standard deviation parameter of the fifth trajectory and the distance standard deviation parameter of the sixth trajectory do not meet the ninth preset condition;

wherein that the parameter of the fifth trajectory and the parameter of the sixth trajectory meet the eighth preset condition comprises: the minimum value of the quantity parameter of the fifth trajectory and the quantity parameter of the sixth trajectory being greater than or equal to the third quantity threshold, and the angle standard deviation parameter of the fifth trajectory and the angle standard deviation parameter of the sixth trajectory being both less than or equal to the third angle standard deviation threshold;

wherein that the distance standard deviation parameter of the fifth trajectory and the distance standard deviation parameter of the sixth trajectory do not meet the ninth preset condition comprises: the distance standard deviation parameter of the fifth trajectory being greater than the first distance standard deviation threshold, and the distance standard deviation parameter of the sixth trajectory being greater than the first distance standard deviation threshold.

13. The method according to claim 5, wherein in the second recognition, the heart rate difference trajectory comprises: the first trajectory, the second trajectory, a seventh trajectory, an eighth trajectory, a ninth trajectory, and a tenth trajectory; and the heart rhythm type is the premature beat when the parameter of the first trajectory and the parameter of the second trajectory meet the second preset condition and a parameter of the seventh trajectory, a parameter of the eighth trajectory, a parameter of the ninth trajectory, and a parameter of the tenth trajectory meet a tenth preset condition;

wherein that the parameter of the first trajectory and the parameter of the second trajectory meet the second preset condition comprises: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than a first standard deviation threshold;

wherein that a parameter of the seventh trajectory, a parameter of the eighth trajectory, a parameter of the ninth trajectory, and a parameter of the tenth trajectory meet a tenth preset condition comprises: a maximum value of an angle standard deviation parameter of the seventh trajectory, an angle standard deviation parameter of the eighth trajectory, an angle standard deviation parameter of the ninth trajectory, and an angle standard deviation parameter of the tenth trajectory being less than or equal to a fourth angle standard deviation threshold.

14. The method according to claim 13, wherein in the second recognition, the heart rate difference trajectory comprises: the first trajectory, the second trajectory, the seventh trajectory, the eighth trajectory, the ninth trajectory, and the tenth trajectory; and the heart rhythm type is the atrial fibrillation when the parameter of the first trajectory and the parameter of the second trajectory meet the second preset condition, the parameter of the seventh trajectory, the parameter of the eighth trajectory, the parameter of the ninth trajectory, and the parameter of the tenth trajectory do not meet the tenth preset condition, and the first probability parameter meets an eleventh preset condition or a first quantity meets a twelfth preset condition;

wherein that the parameter of the first trajectory and the parameter of the second trajectory meet the second preset condition comprises: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

wherein that the parameter of the seventh trajectory, the parameter of the eighth trajectory, the parameter of the ninth trajectory, and the parameter of the tenth trajectory do not meet the tenth preset condition comprises: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold;

wherein that the first probability parameter meets an eleventh preset condition comprises: the first probability parameter being less than a third probability threshold;

wherein that a first quantity meets a twelfth preset condition comprises: the first quantity being greater than or equal to a fourth quantity threshold.

15. The method according to claim 14, wherein in the second recognition, the heart rate difference trajectory comprises: the first trajectory, the second trajectory, the seventh trajectory, the eighth trajectory, the ninth trajectory, and the tenth trajectory; and the heart rhythm type is the sinus rhythm when the parameter of the first trajectory and the parameter of the second trajectory meet the second preset condition, the parameter of the seventh trajectory, the parameter of the eighth trajectory, the parameter of the ninth trajectory, and the parameter of the tenth trajectory do not meet the tenth preset condition, and the first probability parameter does not meet the eleventh preset condition or the first quantity does not meet the twelfth preset condition;

wherein that the parameter of the first trajectory and the parameter of the second trajectory meet the second preset condition comprises: the sum of the quantity parameter of the first trajectory and the quantity parameter of the second trajectory being greater than or equal to the first quantity threshold, and at least one of the angle standard deviation parameter of the first trajectory and the angle standard deviation parameter of the second trajectory being greater than the first standard deviation threshold;

wherein that the parameter of the seventh trajectory, the parameter of the eighth trajectory, the parameter of the ninth trajectory, and the parameter of the tenth trajectory do not meet the tenth preset condition comprises: the maximum value of the angle standard deviation parameter of the seventh trajectory, the angle standard deviation parameter of the eighth trajectory, the angle standard deviation parameter of the ninth trajectory, and the angle standard deviation parameter of the tenth trajectory being greater than the fourth angle standard deviation threshold;

wherein that the first probability parameter does not meet the eleventh preset condition comprises: the first probability parameter being no less than the third probability threshold;

wherein that the first quantity does not meet the twelfth preset condition comprises: the first quantity being less than the fourth quantity threshold.

16. The method according to claim 1, further comprising:

acquiring an ACC signal with a second preset duration of time; and determining a state of the electronic device based on the ACC signal with the second preset duration of time;

wherein the acquiring a first PPG signal with a first preset duration of time comprises:

acquiring the first PPG signal with the first preset duration of time if the electronic device is always in a static state within a third preset duration of time, the third preset duration of time being less than or equal to the second preset duration of time.

17. The method according to claim 1, further comprising:

displaying prompt information to a user when the heart rhythm type is the atrial fibrillation, the prompt information being used for notifying the user of an abnormal heart rhythm.

18. The method of claim 1, wherein time units of at least one of the first preset duration of time, the fourth preset duration of time, or the fifth preset duration of time are hours, minutes, seconds, microseconds, or milliseconds.

19. An electronic device, comprising:

a processor; and a memory coupled to the processor and configured to store a computer program, which when executed by the processor, causes an electronic device to:

acquire a first photoplethysmograph (PPG) signal with a first preset duration of time, wherein the acquiring a first PPG signal with the first preset duration of time comprises:

acquire a PPG signal and an accelerometer (ACC) signal with a fourth preset duration of time, the PPG signal with the first preset duration of time including a plurality of PPG signals with the fourth preset duration of time, the fourth preset duration of time being less than the first preset duration of time, determine whether the electronic device has been in a motion state within a fifth preset duration of time, the fifth preset duration of time being greater than the first preset duration of time, and continuously acquire the PPG signal and the ACC signal with the fourth preset duration of time until an acquisition duration meets the first preset duration of time if the electronic device has not been in the motion state within the fifth preset duration of time;

determine a plurality of heart rate values based on the first PPG signal;

determine a difference of every two adjacent heart rates based on the plurality of heart rate values, the difference of every two adjacent heart rates being used for generating a heart rate difference trajectory graph;

acquire a parameter of a heart rate difference trajectory based on the heart rate difference trajectory graph and the parameter of the heart rate difference trajectory comprising at least one of an angle, a quantity, an angle standard deviation, or a distance standard deviation;

determine a heart rhythm type of the first PPG signal according to the parameter of the heart rate difference trajectory, the heart rhythm type comprising at least one of a premature beat, atrial fibrillation, a sinus rhythm, ventricular tachycardia, bigeminy, or trigeminy; and display the heart rhythm type of the first PPG signal.

20. A chip, comprising:

a memory; and a processor communicatively coupled to the memory, wherein the processor is configured to execute instructions stored in the memory to cause the chip to:

acquire a first photoplethysmograph (PPG) signal with a first preset duration of time, wherein the acquiring a first PPG signal with the first preset duration of time comprises:

acquire a PPG signal and an accelerometer (ACC) signal with a fourth preset duration of time, the PPG signal with the first preset duration of time including a plurality of PPG signals with the fourth preset duration of time, the fourth preset duration of time being less than the first preset duration of time, determine whether an electronic device has been in a motion state within a fifth preset duration of time, the fifth preset duration of time being greater than the first preset duration of time, and continuously acquire the PPG signal and the ACC signal with the fourth preset duration of time until an acquisition duration meets the first preset duration of time if the electronic device has not been in the motion state within the fifth preset duration of time;

determine a plurality of heart rate values based on the first PPG signal;

determine a difference of every two adjacent heart rates based on the plurality of heart rate values, the difference of every two adjacent heart rates being used for generating a heart rate difference trajectory graph;

acquire a parameter of a heart rate difference trajectory based on the heart rate difference trajectory graph and the parameter of the heart rate difference trajectory comprising at least one of an angle, a quantity, an angle standard deviation, or a distance standard deviation;

determine a heart rhythm type of the first PPG signal according to the parameter of the heart rate difference trajectory, the heart rhythm type comprising at least one of a premature beat, atrial fibrillation, a sinus rhythm, ventricular tachycardia, bigeminy, or trigeminy; and display the heart rhythm type of the first PPG signal.

* * * * *